(12) United States Patent
Sanghvi et al.

(10) Patent No.: US 9,283,261 B2
(45) Date of Patent: Mar. 15, 2016

(54) LINACLOTIDE COMPOSITIONS

(71) Applicant: Forest Laboratories Holdings Ltd., Hamilton (BM)

(72) Inventors: Ritesh Sanghvi, Commack, NY (US); Matthew Miller, Kew Gardens, NY (US); Andreas Grill, Hauppauge, NY (US); Yun Mo, Dix Hills, NY (US); Mohammad Mafruhul Bari, Lake Grove, NY (US); Matthew Ronsheim, Port Jefferson, NY (US); Joseph Stainkamp, Holtsville, NY (US)

(73) Assignee: Forest Laboratories Holdings Limited, Hamilton (BM)

( * ) Notice: Subject to any disclaimer, the term of this patent is extended or adjusted under 35 U.S.C. 154(b) by 0 days.

(21) Appl. No.: 14/489,718

(22) Filed: Sep. 18, 2014

(65) Prior Publication Data

US 2015/0005241 A1    Jan. 1, 2015

Related U.S. Application Data

(63) Continuation of application No. 13/799,982, filed on Mar. 13, 2013, now abandoned.

(60) Provisional application No. 61/670,875, filed on Jul. 12, 2012.

(51) Int. Cl.
| | | |
|---|---|---|
| A61K 38/12 | (2006.01) | |
| A61K 38/10 | (2006.01) | |
| C07K 7/08 | (2006.01) | |
| A61K 9/00 | (2006.01) | |
| A61K 47/02 | (2006.01) | |
| A61K 9/16 | (2006.01) | |
| A61K 47/18 | (2006.01) | |
| A61K 47/22 | (2006.01) | |
| A61K 47/26 | (2006.01) | |
| A61K 47/42 | (2006.01) | |

(52) U.S. Cl.
CPC ............... *A61K 38/10* (2013.01); *A61K 9/0053* (2013.01); *A61K 9/1676* (2013.01); *A61K 47/02* (2013.01); *C07K 7/08* (2013.01); *A61K 47/183* (2013.01); *A61K 47/22* (2013.01); *A61K 47/26* (2013.01); *A61K 47/42* (2013.01)

(58) Field of Classification Search
None
See application file for complete search history.

(56) References Cited

U.S. PATENT DOCUMENTS

| | | | | |
|---|---|---|---|---|
| 7,304,036 | B2 * | 12/2007 | Currie et al. | 514/12.2 |
| 7,704,947 | B2 * | 4/2010 | Currie et al. | 514/4.8 |
| 7,745,409 | B2 * | 6/2010 | Currie et al. | 514/1.1 |
| 7,772,188 | B2 * | 8/2010 | Currie et al. | 514/20.6 |
| 8,222,201 | B2 * | 7/2012 | Sanghvi et al. | 514/1.1 |
| 8,507,447 | B2 * | 8/2013 | Currie et al. | 514/21.5 |
| 8,748,573 | B2 * | 6/2014 | Fretzen et al. | 530/327 |
| 8,802,628 | B2 * | 8/2014 | Fretzen et al. | 514/1.1 |
| 8,969,914 | B2 * | 3/2015 | Chalamala et al. | 257/174 |
| 2010/0048489 | A1 * | 2/2010 | Fretzen et al. | 514/14 |
| 2011/0059903 | A1 * | 3/2011 | Fretzen et al. | 514/21.1 |
| 2014/0018307 | A1 * | 1/2014 | Sanghvi et al. | 514/21.1 |

* cited by examiner

*Primary Examiner* — Marcela M Cordero Garcia
(74) *Attorney, Agent, or Firm* — Matthew O. Brady; Thomas F. Poché; Debra D. Condino

(57) ABSTRACT

The present invention is directed to stable linaclotide compositions and methods of treating gastrointestinal disorders in patients in need thereof by providing the stable linaclotide compositions.

22 Claims, 4 Drawing Sheets

LINACLOTIDE COMPOSITIONS

FIELD OF THE INVENTION

This invention relates to linaclotide compositions and methods for treating gastrointestinal disorders.

SEQUENCE LISTING

This application incorporates by reference in its entirety the Sequence Listing entitled "Sequence_listing_ST25" (11.6 kilobytes), which was created Feb. 6, 2015 and filed electronically herewith.

BACKGROUND

U.S. Pat. Nos. 7,304,036 and 7,371,727 disclose peptides that act as agonists of the guanylate cyclase C (GC-C) receptor for the treatment of gastrointestinal disorders. One particular peptide disclosed is linaclotide, which consists of the following amino acid sequence (SEQ ID NO: 1):

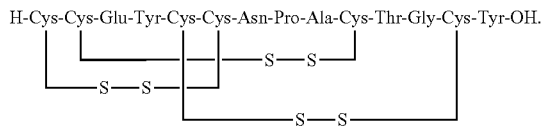

The '036 and '727 patents also disclose methods for preparing linaclotide and related peptides. The contents of these patents are incorporated herein by reference in their entirety.

There remains a need for improved linaclotide compositions that have improved stability against formaldehyde, which can enter linaclotide compositions from a variety of sources.

The present invention seeks to provide such improved linaclotide compositions, as well as methods of treating gastrointestinal disorders by providing the linaclotide compositions to patients in need thereof.

SUMMARY OF THE INVENTION

The present invention relates in some embodiments to stable linaclotide compositions that comprises linaclotide, a sterically hindered primary amine, a divalent metal cation and a formaldehyde scavenger compound.

In some embodiments, the present invention relates to stable linaclotide compositions that comprises linaclotide, a sterically hindered primary amine, a divalent metal cation and a formaldehyde scavenger compound, and a peptide having the structure of formula (I) or a pharmaceutically acceptable salt thereof (SEQ ID NO: 3):

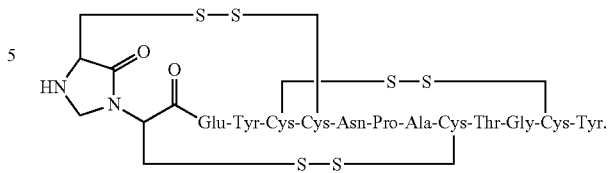

In some embodiments, the present invention relates to stable linaclotide compositions that comprises linaclotide, a sterically hindered primary amine, a divalent metal cation and a formaldehyde scavenger compound, and a peptide having the structure of formula (I) or a pharmaceutically acceptable salt thereof (SEQ ID NO: 2):

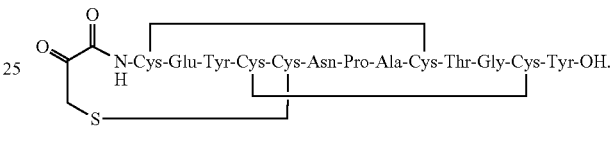

In some embodiments, the present invention relates to stable linaclotide compositions that comprises linaclotide, a sterically hindered primary amine, a divalent metal cation and a formaldehyde scavenger compound, and a peptide having the structure of formula (IV) or a pharmaceutically acceptable salt thereof (SEQ ID NO: 18):

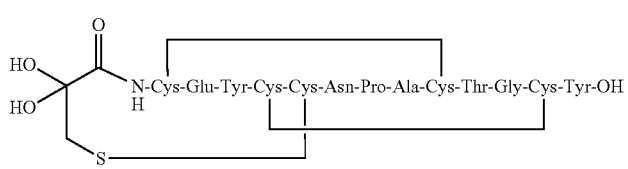

In some embodiments, the present invention relates to stable linaclotide compositions that comprises linaclotide, a sterically hindered primary amine, a divalent metal cation and a formaldehyde scavenger compound, and one or both of the peptide of formula (VI) and the peptide of formula (VII).

In some embodiments, the present invention relates to stable linaclotide compositions that comprises linaclotide, a sterically hindered primary amine, a divalent metal cation, a formaldehyde scavenger compound, a peptide having the structure of formula (I) or a pharmaceutically acceptable salt thereof, and one or both of the peptide of formula (VI) and the peptide of formula (VII).

In some embodiments, the present invention relates to stable linaclotide compositions that comprises linaclotide, a sterically hindered primary amine, a divalent metal cation and a peptide having the following structure of formula (VIII) or a pharmaceutically acceptable salt thereof (SEQ ID NO: 3):

(VIII)

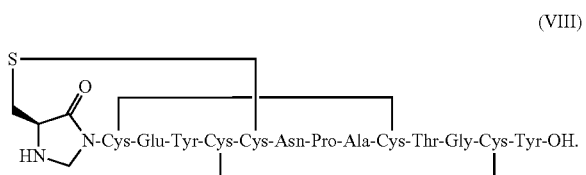

In some embodiments, the present invention relates to stable linaclotide compositions that comprises linaclotide, a sterically hindered primary amine, a divalent metal cation, a formaldehyde scavenger compound, a peptide having the structure of formula (I) and one or both of the peptide of formula (III) and the peptide of formula (IV).

In some embodiments, the present invention relates to stable linaclotide compositions that comprise linaclotide, a sterically hindered primary amine, a divalent metal cation and a formaldehyde scavenger compound, a peptide having the structure of formula (I) or a pharmaceutically acceptable salt thereof (SEQ ID NO: 3):

(I)

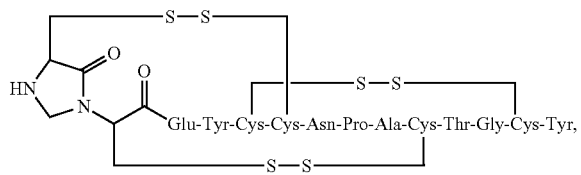

and a peptide having a structure of Formula (II) or a pharmaceutically acceptable salt thereof (SEQ ID NO: 4):

(II)

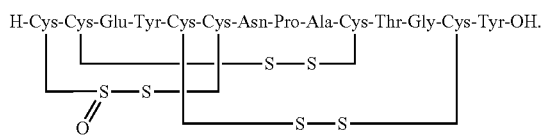

In some embodiments, the present invention relates to stable compositions that comprise linaclotide or a pharmaceutically acceptable salt thereof, a peptide or a pharmaceutically acceptable salt thereof that comprises the amino acid sequence Cys Cys Glu Tyr Cys Cys Asn Pro Ala Cys Thr Gly Cys Tyr (wherein at least one carboxyl group of the peptide is an alkyl ester having the formula (—COOR) in which R is a $C_{1-6}$ alkyl), and one or more formaldehyde scavenger compounds.

In some embodiments, a stable linaclotide composition is provided which comprises linaclotide or a pharmaceutically acceptable salt thereof, a peptide having the structure of formula (I) or a pharmaceutically acceptable salt thereof, and one or more formaldehyde scavenger compounds (SEQ ID NO: 3):

(I)

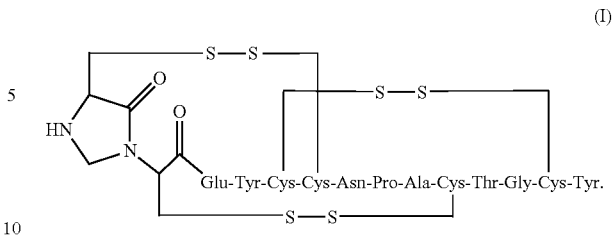

In some embodiments, a stable linaclotide composition is provided which comprises linaclotide or a pharmaceutically acceptable salt thereof, a peptide (e.g., a formaldehyde imine product, e.g., a formaldehyde imine product) having the structure of formula (II) or a pharmaceutically acceptable salt thereof, and one or more formaldehyde scavenger compounds (SEQ ID NO: 8):

(II)

$H_2O$=Cys-Cys-Glu-Tyr-Cys-Cys-Asn-Pro-Ala-Cys-Thr-Gly-Cys-Tyr-OH.

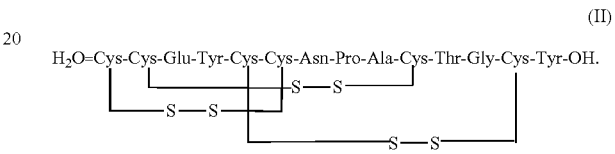

In some embodiments, a stable linaclotide composition is provided which comprises linaclotide, one or more formaldehyde scavenger compound, a first peptide having the structure of formula (I) or a pharmaceutically acceptable salt thereof (SEQ ID NO: 3):

(I)

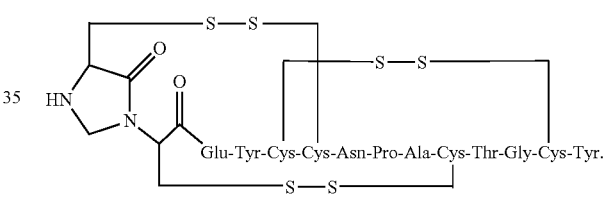

and a second peptide having the structure of Formula (II) or a pharmaceutically acceptable salt thereof (SEQ ID NO: 4):

(II)

H-Cys-Cys-Glu-Tyr-Cys-Cys-Asn-Pro-Ala-Cys-Thr-Gly-Cys-Tyr-OH.

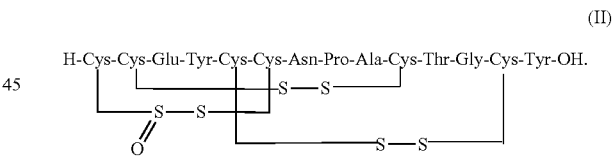

In some embodiments, a stable linaclotide composition is provided which comprises linaclotide, one or more formaldehyde scavenger compound, a first peptide having the structure of formula (I) or a pharmaceutically acceptable salt thereof, and one or both of (i) a peptide having the structure of formula (III) and (ii) a peptide having the structure of formula (IV).

In some embodiments, the linaclotide composition comprises a linaclotide peptide comprising the amino acid sequence Cys Cys Glu Tyr Cys Cys Asn Pro Ala Cys Thr Gly Cys Tyr which is modified with the addition of methylene at the α-amine group of the N-terminal $Cys_1$ which is cross-linked to the amine group of $Cys_2$ to form an imidazolidinone 5 membered ring at the N-terminus of the peptide ("$Cys_1$-IMD"), wherein "$Cys_1$-IMD" refers to the linaclotide imidazolidinone derivative modified on its N-terminal amine group (SEQ ID NO: 3). In some embodiments, the imine modification may be produced by a formaldehyde mediated reaction in the presence of acid catalyst.

In some embodiments, stable compositions are provided which comprise linaclotide or a pharmaceutically acceptable salt thereof, a peptide having the structure of formula (III) or a pharmaceutically acceptable salt thereof, and one or more formaldehyde scavenger compounds (SEQ ID NO: 19):

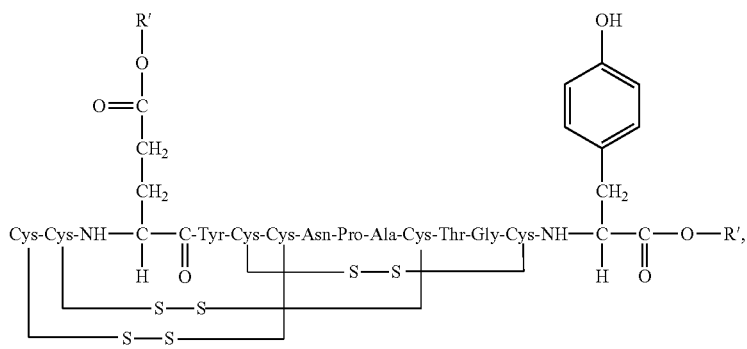

(III)

wherein R' is H or a $C_{1-6}$ alkyl, and at least one R' is $C_{1-6}$ alkyl.

In some embodiments, stable compositions are provided which comprise linaclotide or a pharmaceutically acceptable salt thereof, a peptide having the structure of formula (IV) or a pharmaceutically acceptable salt thereof, and one or more formaldehyde scavenger compounds (SEQ ID NO: 6):

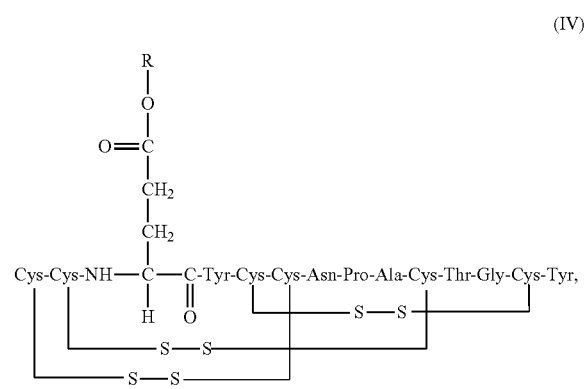

(IV)

wherein R is a $C_{1-6}$ alkyl.

In some embodiments, stable compositions are provided which comprise linaclotide or a pharmaceutically acceptable salt thereof, a peptide having the structure of formula (V) or a pharmaceutically acceptable salt thereof, and one or more formaldehyde scavenger compounds (SEQ ID NO: 7):

Another aspect of the present invention provides a method for treating a gastrointestinal disorder, which includes providing the linaclotide composition to a patient diagnosed with a gastrointestinal disorder.

The details of one or more embodiments of the invention are set forth in the accompanying description.

Figure 1:
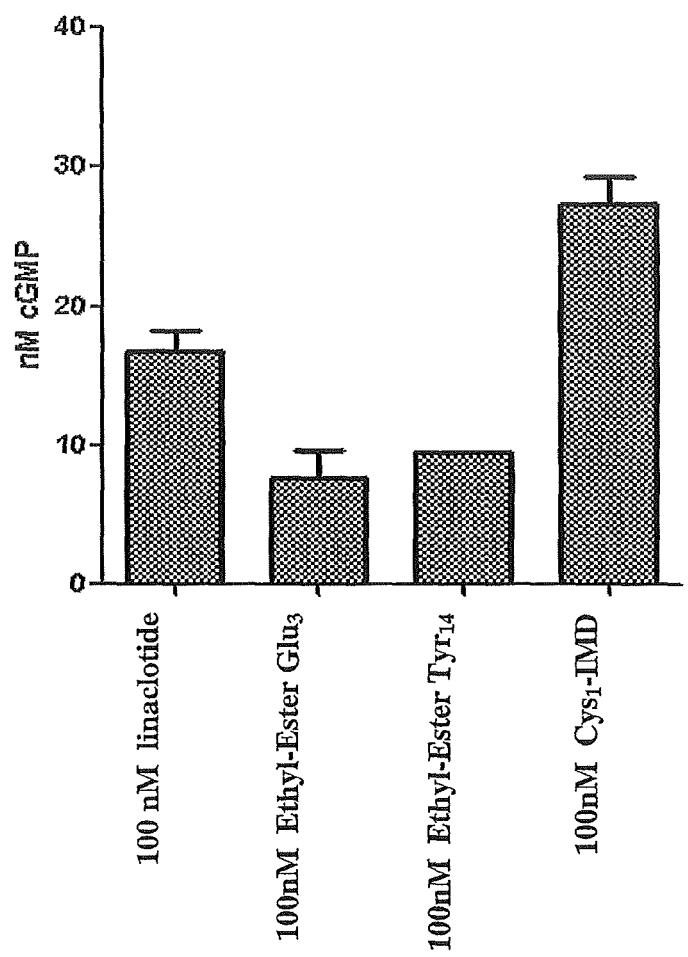
FIG. 1 shows the dose response of exemplary peptides of the present invention in a T84 cell c-GMP assay.

The figures are provided by way of example and are not intended to limit the scope of the present invention.

DETAILED DESCRIPTION

Guanylate cyclase C (GC-C) is a transmembrane receptor that is located on the apical surface of epithelial cells in the stomach and intestine. The receptor has an extracellular ligand-binding domain, a single transmembrane region and a C-terminal guanylyl cyclase domain. When a ligand binds to the extracellular domain of GC-C, the intracellular catalytic domain catalyzes the production of cGMP from GTP. In vivo, this increase in intracellular cGMP initiates a cascade of (V)

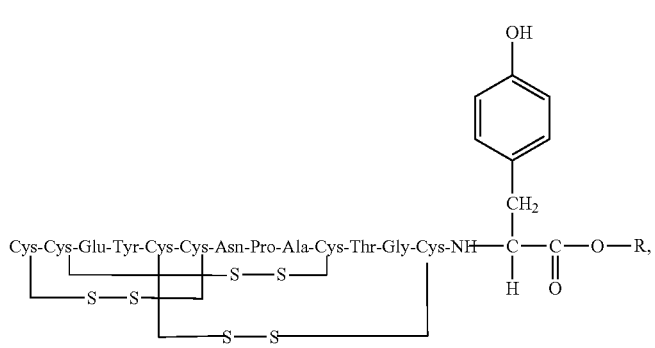

wherein R is $C_{1-6}$ alkyl.

events that leads to increased secretion of chloride and bicarbonate into the intestinal lumen, increased luminal pH, decreased luminal sodium absorption, increased fluid secretion, and acceleration of intestinal transit. cGMP is secreted bidirectionally from the epithelium into the mucosa and lumen. The peptides and compositions of the present invention bind to the intestinal GC-C receptor which is a regulator of fluid and electrolyte balance in the intestine.

Formaldehyde Scavenger Compounds

It has been discovered that the stability of linaclotide compositions can be increased to a surprisingly high degree by including in the linaclotide composition a suitable/appropriate amount of one or more formaldehyde scavenger compounds.

While not wishing to be bound by any theory, it is believed that the formaldehyde scavenger compounds increase linaclotide stability by reacting with formaldehyde in such a manner that the formaldehyde has a lesser capacity/ability to react with linaclotide. In this regard, the formaldehyde scavenger compound can be any compound that reduces exposure of the linaclotide to formaldehyde in the composition, such as by reacting or interacting with at least a portion of formaldehyde that enters the linaclotide composition or gets proximate to linaclotide. Such formaldehyde can enter the linaclotide composition from a variety of sources and otherwise have deleterious effects on linaclotide and drug product stability.

In some preferred embodiments, the formaldehyde scavenger compound comprises a nitrogen center that is reactive with formaldehyde, such as to form one or more reversible or irreversible bonds between the formaldehyde scavenger compound and the formaldehyde (preferably in some embodiments one or more irreversible covalent bonds). For example, in some preferred embodiments, the formaldehyde scavenger compound comprises one or more nitrogen atoms/centers that are reactive with formaldehyde to form a schiff base imine that is capable of subsequently binding with formaldehyde. In some preferred embodiments, the formaldehyde scavenger compound(s) comprise one or more nitrogen centers that are reactive with formaldehyde to form one or more 5-8 member cyclic rings. In this regard, the formaldehyde scavenger compound preferably comprises one or more amine or amide groups. For example, the formaldehyde scavenger compound can be an amino acid, an amino sugar, an alpha amine compound, or a conjugate or derivative thereof, or a mixture thereof. In some preferred embodiments, the formaldehyde scavenger compound comprises two or more amines and/or amides.

It has also been surprisingly discovered in some embodiments, that formaldehyde scavenger compounds that comprise multiple amine binding sites achieve surprisingly high stabilizing effects on linaclotide as is demonstrated in Example 5. For example, some preferred formaldehyde scavenger compounds comprise one or more (e.g., two or more) primary amines. These include, for example, glycine, alanine, serine, threonine, cysteine, valine, lecuine, isoleucine, methionine, phenylalanine, tyrosine, aspartic acid, glutamic acid, arginine, lysine, ornithine, citrulline, taurine pyrrolysine, or a conjugate or mixture thereof.

In some especially preferred embodiments, the formaldehyde scavenger compound(s) comprises one or more secondary amines (which have been found in some embodiments to have higher reactivity with formaldehyde and thus higher stabilizing effects on linaclotide drug products). Some especially preferred formaldehyde scavenger compounds comprise two or more secondary amines. These include, for example, megulmine, histidine, aspartame, proline, tryptophan, citrulline, pyrrolysine, or a conjugate or mixture thereof.

Other preferred formaldehyde scavenger compounds comprise one or more (e.g., two or more) primary amines and one or more (e.g., two or more) secondary amines. These include, for example, arginine, citrulline, pyrrolysine, or a conjugate or mixture thereof.

Moreover, the formaldehyde scavenger compounds can comprise one or more amide groups. For example, the scavenger compound can be asparagine, glutamine, citrulline, or a conjugate or mixture thereof.

The formaldehyde scavenger compound can be introduced into the linaclotide composition in any suitable form. For example, the scavenger can be lyophilized. Alternatively, or in addition, the formaldehyde scavenger compound can be applied (e.g., sprayed) onto beads before being introduced into the linaclotide composition. These beads can be made of any suitable material, such as for example cellulose, glass, sugar(s) or a combination or mixture thereof.

In some embodiments, it has been surprisingly found (see Example 5) that formaldehyde scavenger compounds may have higher stabilizing effects on linaclotide when the formaldehyde scavenger compound used is in amorphous form. Therefore, in some especially preferred embodiments, the formaldehyde scavenger compound is amorphous.

Lastly, the formaldehyde scavenger compound can be present in the linaclotide composition in any suitable amount. In some preferred embodiments, the linaclotide composition comprises a ratio of scavenger to leucine between about 10:1 and about 1:1, preferably between about 7:1 and about 1:1, even more preferably between about 5:1 and about 1:1 or even between about 3:1 and about 1:1.

Exemplary Peptides in the Linaclotide Composition:

The linaclotide compositions may further comprise one or more of the peptides described herein.

In various embodiments, the linaclotide composition comprises a peptide that is modified wherein at least one carboxyl group of the amino acid residue of the peptide is modified to an alkyl ester. This modification may be produced, for example, by treating a carboxylic acid with an alcohol in the presence of a dehydrating agent wherein the dehydrating agent can include but is not limited to a strong acid such as sulfuric acid. Other methods of producing alkyl esters from carboxyl groups are readily known in those skilled in the arts and are incorporated herein.

As used herein, a carboxyl group has the formula: (—COOH).

As used herein, the term "alkyl", refers to a saturated linear or branched-chain monovalent hydrocarbon radical.

As used herein, a group is terminal or terminus when the group is present at the end of the amino acid sequence.

As used herein, an amine group on a peptide has the formula:

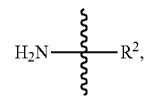

wherein $R^2$ is the rest of the peptide.

As used herein, an imine group on a peptide has the formula:

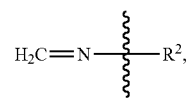

wherein $R^2$ is the rest of the peptide.

In some embodiments, the carboxylic acid of the side chain of a glutamate amino acid in a peptide sequence is modified into an alkyl ester.

In further embodiments, the carboxylic acid on the side chain of a glutamate amino acid a peptide sequence is modified into an ethyl ester.

In other embodiments, the C-terminus carboxylic acid of a tyrosine amino acid in a peptide sequence is modified into an alkyl ester.

In further embodiments, the C-terminus carboxylic acid of a tyrosine amino acid of a peptide sequence is modified into an ethyl ester.

In some embodiments, the linaclotide composition comprises a peptide or a pharmaceutically acceptable salt thereof, wherein the peptide comprises the amino acid sequence Cys Cys Glu Tyr Cys Cys Asn Pro Ala Cys Thr Gly Cys Tyr, wherein at least one carboxyl group of the peptide is an alkyl ester having the formula (—COOR) in which R is a $C_{1-6}$ alkyl.

In several embodiments, the linaclotide composition comprises a peptide having an amino acid structure of (SEQ ID NO: 19):

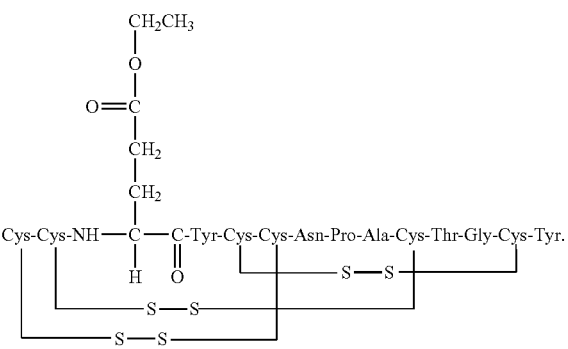

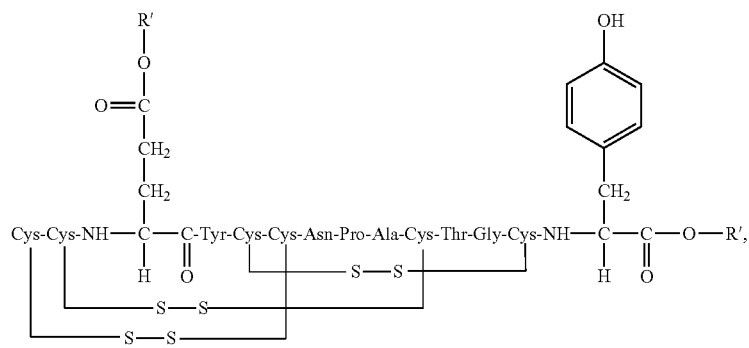

or a pharmaceutically acceptable salt thereof, wherein R' is H or a $C_{1-6}$ alkyl, and at least one R' is $C_{1-6}$ alkyl.

In some embodiments, the linaclotide composition comprises a peptide having an amino acid structure of (SEQ ID NO: 6):

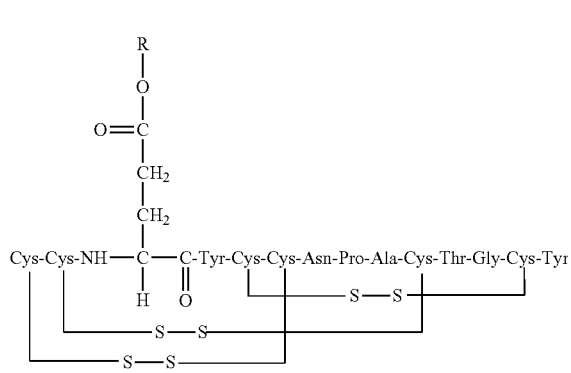

wherein R is a $C_{1-6}$ alkyl ("$Glu_3$-alkyl ester").

In other embodiments, R is a $C_{1-4}$ alkyl.

In further embodiments, R is methyl, ethyl, or propyl.

In some embodiments, the linaclotide composition comprises a peptide having an amino acid structure of ("$Glu_3$-ethyl ester") (SEQ ID NO: 10):

In some embodiments, the linaclotide composition comprises a peptide having an amino acid structure of (SEQ ID NO: 11):

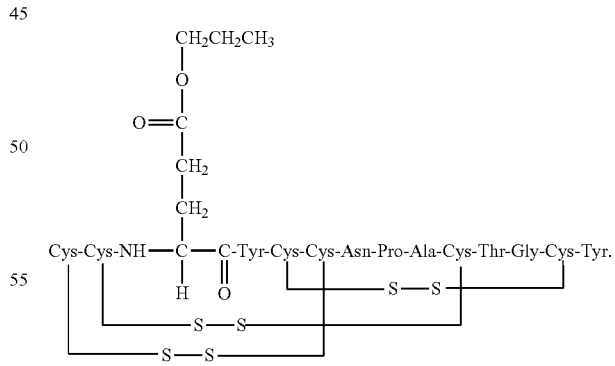

In some embodiments, the linaclotide composition comprises a peptide having an amino acid structure of (SEQ ID NO: 9):

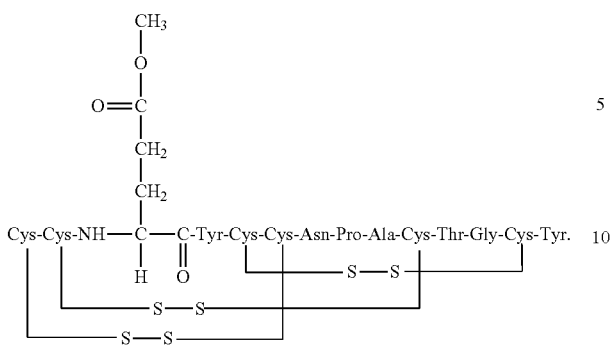

In some embodiments, the C-terminal tyrosine of the Glu₃-alkyl ester or pharmaceutically acceptable salt is absent.

In some embodiments, the linaclotide composition comprises a peptide having an amino acid structure of (SEQ ID NO: 7):

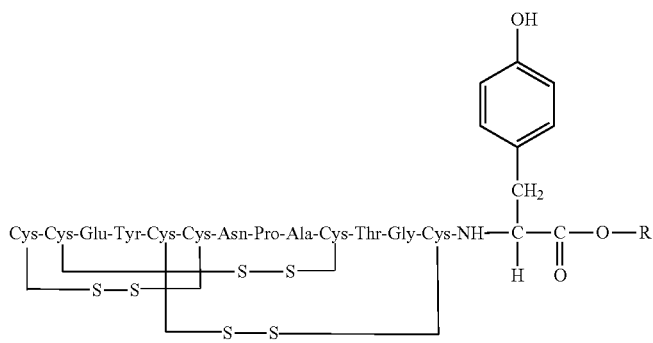

wherein R is $C_{1-6}$ alkyl.

In other embodiments, R is a $C_{1-4}$ alkyl.

In further embodiments, R is methyl, ethyl, or propyl.

In some embodiments, the linaclotide composition comprises a peptide having an amino acid structure of ("Tyr₁₄-ethyl ester") (SEQ ID NO: 13):

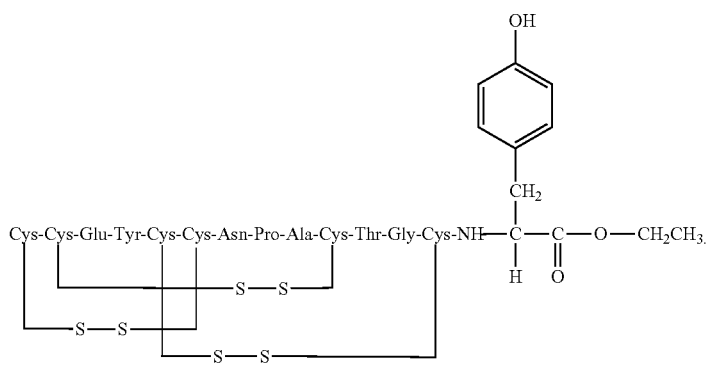

In some embodiments, the linaclotide composition comprises a peptide having an amino acid structure of (SEQ ID NO: 14):

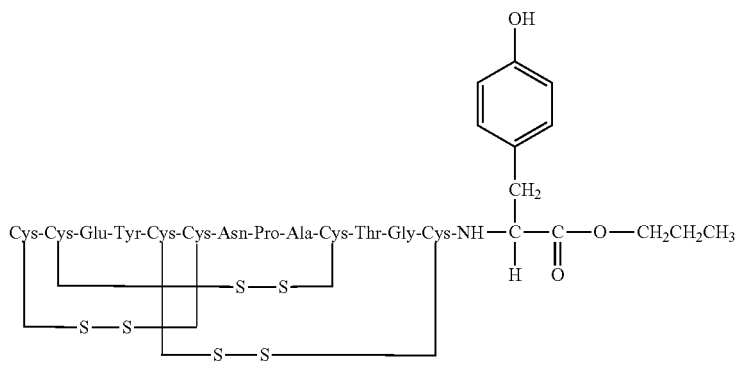

In some embodiments, the linaclotide composition comprises a peptide having an amino acid structure of (SEQ ID NO: 12):

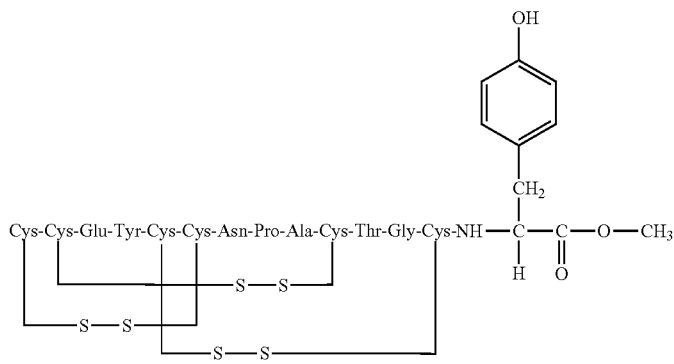

In addition, the linaclotide composition may comprise a peptide that is modified wherein at least one amine group of the amino acid residues of the peptide is modified into an imine. This modification may be produced, for example, by treating an amine group with a carbonyl, such as an aldehyde or ketone, in the presence of acid catalyst. Other methods of producing imines from amine groups are readily known to those skilled in the arts and are incorporated herein.

In some embodiments, the imine modification may be produced by a formaldehyde mediated reaction in the presence of acid catalyst.

In further embodiments, the linaclotide composition comprises a peptide having an imine carbon that is cross-linked to another amine group of the peptide.

In other embodiments, the linaclotide composition comprises a peptide that is modified into an imine at the α-amine group of the N-terminal amino acid, wherein the imine carbon is cross-linked with an amine group of the second amino acid residue of the peptide forming a five membered ring.

In other embodiments, the linaclotide composition comprises a peptide having the amino acid sequence Cys Cys Glu Tyr Cys Cys Asn Pro Ala Cys Thr Gly Cys Tyr wherein the peptide may be modified with the addition of methylene at the α-amine group of the N-terminal Cys$_1$ which is cross-linked to the amine group of Cys$_2$ to form an imidazolidinone 5 membered ring at the N-terminus of the peptide ("Cys$_1$-MD") (SEQ ID NO: 3).

In several embodiments, the linaclotide composition comprises a peptide or a pharmaceutically acceptable salt thereof, wherein the peptide comprising the amino acid sequence Cys Cys Glu Tyr Cys Cys Asn Pro Ala Cys Thr Gly Cys Tyr, wherein at least one amine group of the peptide is an imine having the formula

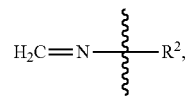

wherein $R^2$ is the rest of the peptide (SEQ ID NO: 8).

In some embodiments, the linaclotide composition comprises a peptide or a pharmaceutically acceptable salt comprises a peptide wherein the N-terminal amine group of the peptide is an imine having the formula

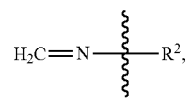

wherein $R^2$ is the rest of the peptide.

In further embodiments, the linaclotide composition comprises a peptide or pharmaceutically acceptable salt thereof comprising an amino acid structure of (SEQ ID NO: 8):

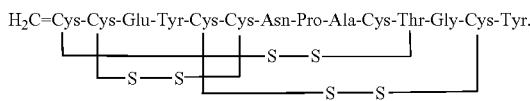

In several embodiments, the linaclotide composition comprises a peptide or pharmaceutically acceptable salt thereof comprising an amino acid structure of (SEQ ID NO: 3):

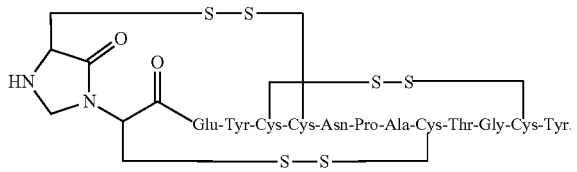

In some embodiments, the C-terminal tyrosine of the $Cys_1$-IMD peptide or pharmaceutically acceptable salt thereof is absent. In some embodiments, the $Cys_1$-IMD peptide or pharmaceutically acceptable salt thereof further comprises one or more peptide modifications, wherein at least one carboxyl group of the peptide is an alkyl ester having the formula (—COOR) in which R is a $C_{1-6}$ alkyl.

In several embodiments, the linaclotide composition comprises a peptide or a pharmaceutically acceptable salt thereof, wherein the peptide consists of the amino acid sequence Cys Cys Glu Tyr Cys Cys Asn Pro Ala Cys Thr Gly Cys Tyr, wherein at least one carboxyl group of the peptide is an alkyl ester having the formula (—COOR) in which R is a $C_{1-6}$ alkyl.

In some embodiments, the linaclotide composition comprises linaclotide, a sterically hindered primary amine, a divalent metal cation and a formaldehyde scavenger compound, and a peptide having the structure of formula (I) or a pharmaceutically acceptable salt thereof (SEQ ID NO: 2):

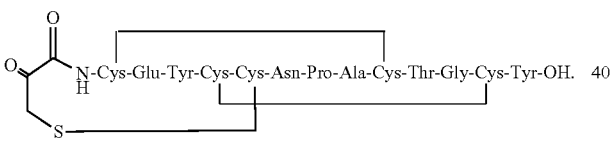

(VI)

In some embodiments, the linaclotide composition comprises linaclotide, a sterically hindered primary amine, a divalent metal cation and a formaldehyde scavenger compound, and a peptide having the structure of formula (IV) or a pharmaceutically acceptable salt thereof (SEQ ID NO 18):

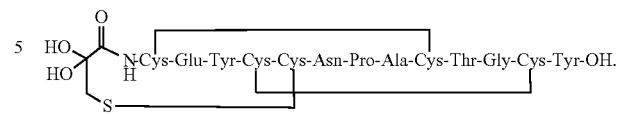

(VII)

In some embodiments, the linaclotide composition comprises linaclotide, a sterically hindered primary amine, a divalent metal cation and a formaldehyde scavenger compound, and one or both of the peptide of formula (VI) and the peptide of formula (VII).

In some embodiments, the linaclotide composition comprises linaclotide, a sterically hindered primary amine, a divalent metal cation, a formaldehyde scavenger compound, a peptide having the structure of formula (I) or a pharmaceutically acceptable salt thereof, and one or both of the peptide of formula (VI) and the peptide of formula (VII).

In some embodiments, the linaclotide composition comprises linaclotide, a sterically hindered primary amine, a divalent metal cation, a formaldehyde scavenger compound, a peptide having the following structure of formula (VIII) or a pharmaceutically acceptable salt thereof (SEQ ID NO: 3):

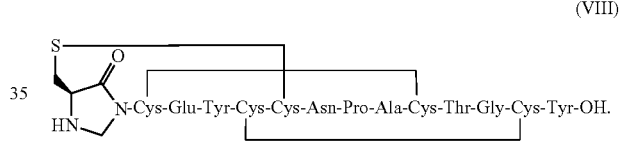

(VIII)

In several embodiments, the linaclotide composition comprises a peptide that consists of an amino acid structure of (SEQ ID NO: 19):

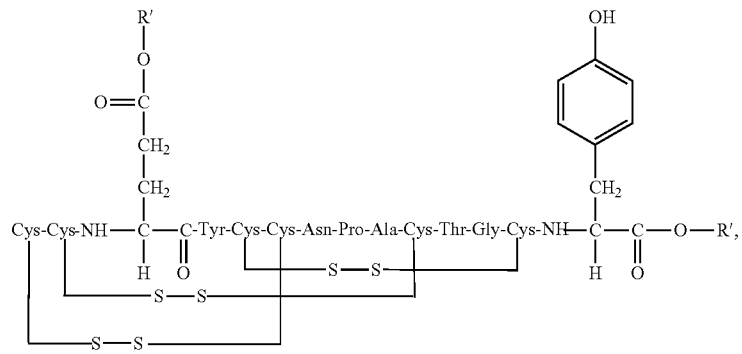

or a pharmaceutically acceptable salt thereof, wherein R' is H or a $C_{1-6}$ alkyl, and at least one R' is $C_{1-6}$ alkyl.

In some embodiments, the linaclotide composition comprises a peptide or pharmaceutically acceptable salt thereof that consists of an amino acid structure of (SEQ ID NO: 6):

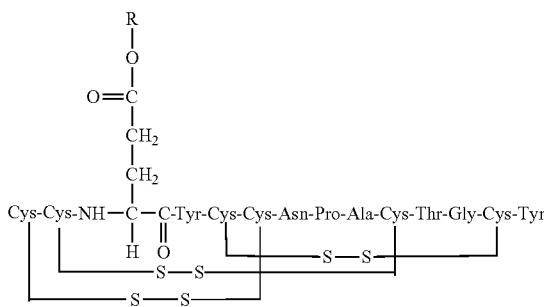

wherein R is a $C_{1-6}$ alkyl. In further embodiments, the C-terminal tyrosine is absent.

In other embodiments, R is a $C_{1-4}$ alkyl.

In further embodiments, R is methyl, ethyl, or propyl.

In some embodiments, the linaclotide composition comprises a peptide or pharmaceutically acceptable salt thereof that consists of a peptide having an amino acid structure of (SEQ ID NO: 10):

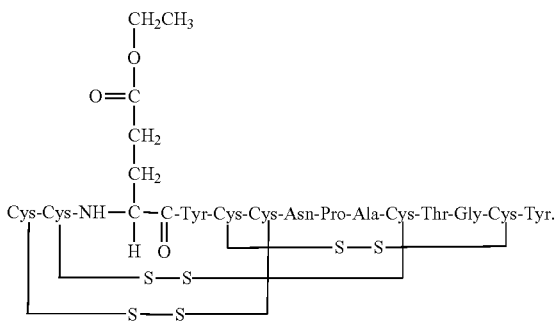

In some embodiments, the linaclotide composition comprises a peptide or pharmaceutically acceptable salt thereof that consists of a peptide having an amino acid structure of (SEQ ID NO: 11):

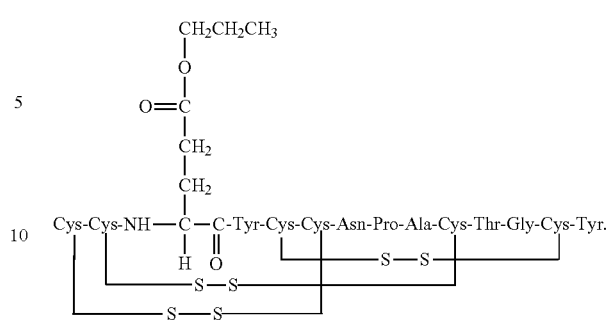

In some embodiments, the linaclotide composition comprises a peptide or pharmaceutically acceptable salt thereof that consists of a peptide having an amino acid structure of (SEQ ID NO: 9):

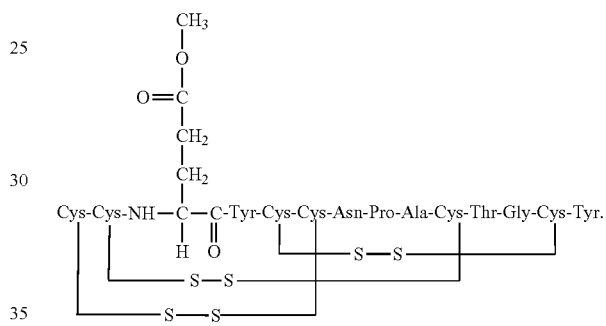

In some embodiments, the linaclotide composition comprises a peptide or pharmaceutically acceptable salt thereof wherein the peptide has an amino acid structure of (SEQ ID NO: 7):

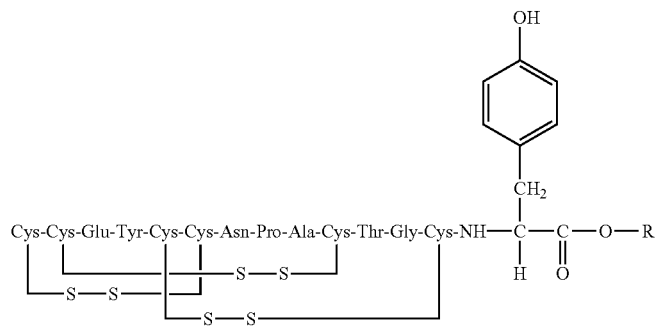

wherein R is $C_{1-6}$ alkyl.

In other embodiments, R is a $C_{1-4}$ alkyl.

In further embodiments, R is methyl, ethyl, or propyl.

In some embodiments, the linaclotide composition comprises a peptide or pharmaceutically acceptable salt thereof that consists of an amino acid structure of (SEQ ID NO:13):

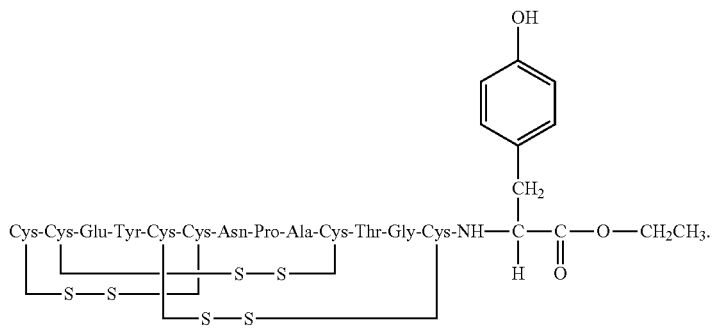

In some embodiments, the linaclotide composition comprises a peptide or pharmaceutically acceptable salt thereof that consists of an amino acid structure of (SEQ ID NO: 14):

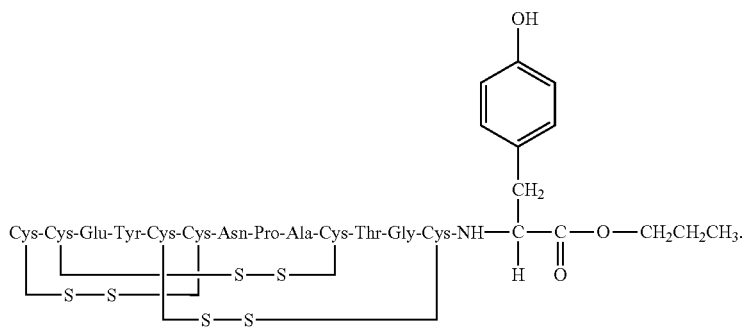

In some embodiments, the linaclotide composition comprises a peptide or pharmaceutically acceptable salt thereof that consists of an amino acid structure of (SEQ ID NO: 12):

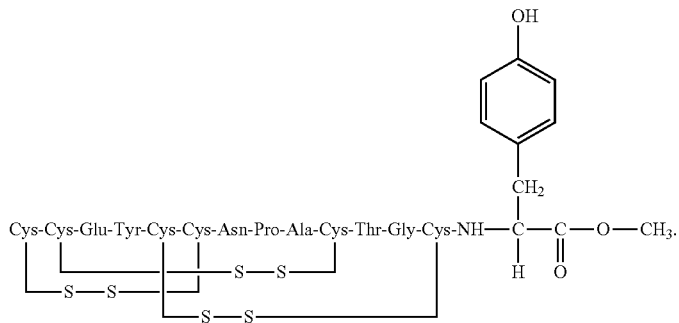

In several embodiments, the linaclotide composition comprises a peptide or a pharmaceutically acceptable salt thereof, wherein the peptide consists of the amino acid sequence Cys Cys Glu Tyr Cys Cys Asn Pro Ala Cys Thr Gly Cys Tyr, wherein at least one amine group of the peptide is an imine having the formula

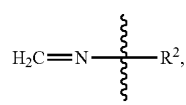

wherein $R^2$ is the rest of the peptide (SEQ ID NO: 8).

In some embodiments, the linaclotide composition comprises a peptide or a pharmaceutically acceptable salt thereof having the structure of formula (III) (SEQ ID NO: 2):

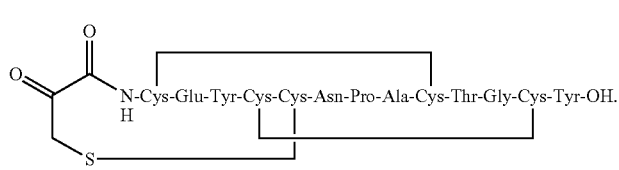

(III)

In some embodiments, the linaclotide composition comprises a peptide or a pharmaceutically acceptable salt thereof having the structure of formula (IV) (SEQ ID NO: 18):

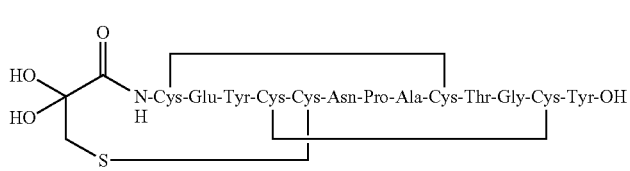

(IV)

In some embodiments, the linaclotide composition comprises one or both of a peptide or a pharmaceutically acceptable salt thereof having the structure of formula (III) and a peptide having the structure of formula (IV).

In some embodiments, the linaclotide composition comprises a peptide or a pharmaceutically acceptable salt thereof having the structure of formula (III) and a peptide or a pharmaceutically acceptable salt thereof having the structure of formula (IV).

In some embodiments, the linaclotide composition comprises a peptide or a pharmaceutically acceptable salt that consists of a peptide wherein the N-terminal amine group of the peptide is an imine having the formula

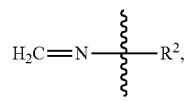

wherein $R^2$ is the rest of the peptide.

In further embodiments, the linaclotide composition comprises a peptide or pharmaceutically acceptable salt thereof that consists of an amino acid structure of (SEQ ID NO: 8):

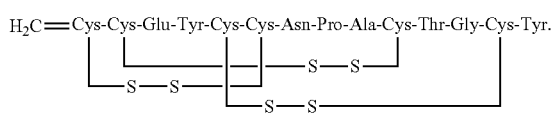

In some embodiments, the linaclotide composition comprises a peptide or pharmaceutically acceptable salt thereof that consists of an amino acid structure of (SEQ ID NO 3):

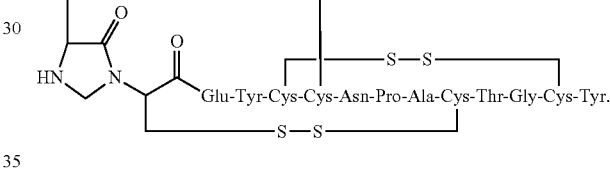

In some embodiments, the linaclotide composition comprises the $Cys_1$-IMD peptide or pharmaceutically acceptable salt wherein the C-terminal tyrosine of the $Cys_1$-IMD peptide or pharmaceutically acceptable salt thereof is absent. In some embodiments, the $Cys_1$-IMD peptide or pharmaceutically acceptable salt thereof further comprises one or more peptide modifications, e.g., wherein at least one carboxyl group of the peptide is an alkyl ester having the formula (—COOR), wherein R is a $C_{1-6}$ alkyl.

Production of Peptides

The peptides or precursor peptides described herein can be produced in any suitable manner such as recombinantly in any known protein expression system, including, without limitation, bacteria (e.g., *E. coli* or *Bacillus subtilis*), insect cell systems (e.g., Drosophila Sf9 cell systems), yeast cell systems (e.g., *S. cerevisiae, S. saccharoinyces*) or filamentous fungal expression systems, or animal cell expression systems (e.g., mammalian cell expression systems). Peptides or precursor peptides of the invention may also be chemically synthesized.

If the peptide or variant peptide is to be produced recombinantly, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally-occurring bacterial ST peptide. The secreted, mature peptide can be purified from the culture medium.

The sequence encoding a peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B. subtilis, Pseudomonas* and *Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide described herein can also be fused to a nucleic acid encoding a peptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants described herein in protein expression systems other than bacteria, and well known to those skilled in the art, can also be used to produce peptides in a biological system.

In other embodiments, peptides containing amino acids not normally incorporated by the translation machinery and described above (e.g.—β-carboxylated Asp, γ-carboxylated Glu, Asu, Aad and Apm) may be recombinantly produced by tRNA modification methods. Methods for modifying tRNA including, but not limited to, modifying the anti-codon, the amino acid attachment site, and/or the accepter stem to allow incorporation of unnatural and/or arbitrary amino acids are known in the art (Biochem. Biophys. Res. Comm. (2008) 372: 480-485; Chem. Biol. (2009) 16:323-36; Nat. Methods (2007) 4:239-44; Nat. Rev. Mol. Cell Biol. (2006) 7:775-82; Methods (2005) 36:227-238; Methods (2005) 36:270-278; Annu. Rev. Biochem. (2004) 73:147-176; Nuc. Acids Res. (2004) 32:6200-6211; Proc. Natl. Acad. Sci. USA (2003) 100:6353-6357; Royal Soc. Chem. (2004) 33:422-430).

In some embodiments, peptides may be chemically produced. Peptides can be synthesized by a number of different methods including solution and solid phase synthesis using traditional BOC or FMOC protection. For example, the peptide can be synthesized on 2-Chlorotrityl or Wang resin using consecutive amino acid couplings. The following protecting groups can be used: Fluorenylmethyloxycarbonyl or tert-butyloxycarbonyl (alpha-amino groups, N-terminus); trityl or tert-butyl (thiol groups of Cys); tert-butyl (γ-carboxyl of glutamic acid and the hydroxyl group of threonine, if present); and trityl (β-amid function of the asparagine side chain and the phenolic group of tyrosine, if present). Coupling can be effected with DIC and HOBt in the presence of a tertiary amine, and the peptide can be deprotected and cleaved from the solid support in using cocktail K (trifluoroacetic acid 81%, phenol 5%, thioanisole 5%, 1,2-ethanedithiol 2.5%, water 3%, dimethylsulphide 2%, ammonium iodide 1.5% w/w). After removal of trifluoroacetic acid and other volatiles the peptide can be precipitated using an organic solvent. Disulfide bonds between Cys residues can be formed using dimethyl sulfoxide (Tam et al. (1991) J. Am. Chem. Soc. 113:6657-62) or using an air oxidation strategy. The resulting peptide can be purified by reverse-phase chromatography and lyophilized.

These peptides can be made, isolated or used either in form of the base or as pharmaceutically acceptable salts thereof. Examples of salts include, without limitation, acetate, chloride, sulfate and phosphate salts of the peptide.

In some embodiments, the linaclotide composition comprises linaclotide or a pharmaceutically acceptable salt and a two or more peptides selected from:

i. a peptide or a pharmaceutically acceptable salt thereof, wherein the peptide comprises the amino acid structure of (SEQ ID NO: 2):

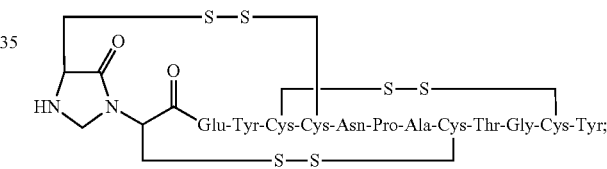

ii. a peptide or a pharmaceutically acceptable salt thereof, wherein the peptide comprises an amino acid structure of (SEQ ID NO: 1):

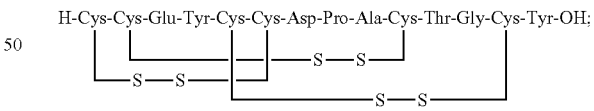

and iii. a peptide or a pharmaceutically acceptable salt thereof, wherein the peptide comprises the amino acid sequence Cys Cys Glu Tyr Cys Cys Asn Pro Ala Cys Thr Gly Cys Tyr, wherein at least one carboxyl group of the peptide is an alkyl ester having the formula (—COOR) in which R is a $C_{1-6}$ alkyl.

In other embodiments, the linaclotide composition comprises linaclotide or a pharmaceutically acceptable salt thereof, one or more formaldehyde scavenger compounds, and a peptide or a pharmaceutically acceptable salt thereof, wherein the peptide comprises an amino acid structure of formula (I) (SEQ ID NO: 3):

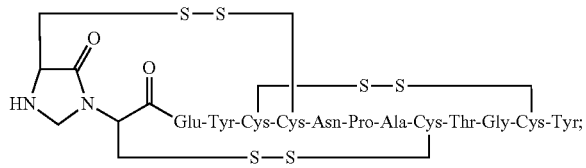

wherein the linaclotide composition contains up to 10%, 20%, 30%, 40%, 50%, 60%, 70%, 80%, or 90% by weight of the peptide of formula (I) as compared to the weight of linaclotide. In some preferred embodiments, the linaclotide composition contains up to 8% by weight of the peptide of formula (I) as compared to the weight of linaclotide. In some preferred embodiments, the linaclotide composition contains up to 7% by weight of the peptide of formula (I) as compared to the weight of linaclotide. In some preferred embodiments, the linaclotide composition contains up to 6% by weight of the peptide of formula (I) as compared to the weight of linaclotide. In some preferred embodiments, the linaclotide composition contains up to 5% by weight of the peptide of formula (I) as compared to the weight of linaclotide. In some preferred embodiments, the linaclotide composition contains up to 4% by weight of the peptide of formula (I) as compared to the weight of linaclotide. In some preferred embodiments, the linaclotide composition contains up to 3% by weight of the peptide of formula (I) as compared to the weight of linaclotide. In some preferred embodiments, the linaclotide composition contains up to 2% by weight of the peptide of formula (I) as compared to the weight of linaclotide. In some preferred embodiments, the linaclotide composition contains up to 1% by weight of the peptide of formula (I) as compared to the weight of linaclotide. In some preferred embodiments, the linaclotide composition contains up to 0.75% by weight of the peptide of formula (I) as compared to the weight of linaclotide. In some preferred embodiments, the linaclotide composition contains up to 0.5% by weight of the peptide of formula (I) as compared to the weight of linaclotide.

In some preferred embodiments, the linaclotide composition contains one or more formaldehyde scavenger compounds and an oral pharmaceutical dosage form that comprises linaclotide and the peptide of formula (I) wherein the peptide of formula (I) is present in the oral pharmaceutical dosage form in an amount of about 0.001 to about 2 wt. % relative to the total weight of the dosage form.

In some preferred embodiments, the linaclotide composition contains one or more formaldehyde scavenger compounds and an oral pharmaceutical dosage form that comprises linaclotide and the peptide of formula (I) wherein the peptide of formula (I) is present in the oral pharmaceutical dosage form in an amount of about 0.001 to about 1 wt. % relative to the total weight of the dosage form.

In some preferred embodiments, the linaclotide composition contains one or more formaldehyde scavenger compounds and an oral pharmaceutical dosage form that comprises linaclotide and the peptide of formula (I) wherein the peptide of formula (I) is present in the oral pharmaceutical dosage form in an amount of about 0.001 to about 0.75 wt. % relative to the total weight of the dosage form.

In some preferred embodiments, the linaclotide composition contains one or more formaldehyde scavenger compounds and an oral pharmaceutical dosage form that comprises linaclotide and the peptide of formula (I) wherein the peptide of formula (I) is present in the oral pharmaceutical dosage form in an amount of about 0.001 to about 0.5 wt. % relative to the total weight of the dosage form.

In some embodiments, the imidazolidinone derivative of linaclotide comprises up to about 15% by weight of the linaclotide composition, up to about 10% by weight of the linaclotide composition, up to about 7% by weight of the linaclotide composition or up to about 5% by weight of the linaclotide composition. In other exemplary embodiments, the imidazolidinone derivative of linaclotide comprises from about 0.01% to about 15% by weight of the linaclotide composition, about 0.05% to about 10% by weight of the linaclotide composition, about 0.05% to about 7% by weight of the linaclotide composition or about 0.05% to about 5% by weight of the linaclotide composition.

In other embodiments, the linaclotide composition comprises linaclotide and a peptide or a pharmaceutically acceptable salt thereof, wherein the peptide comprises an amino acid structure of (SEQ ID NO: 13):

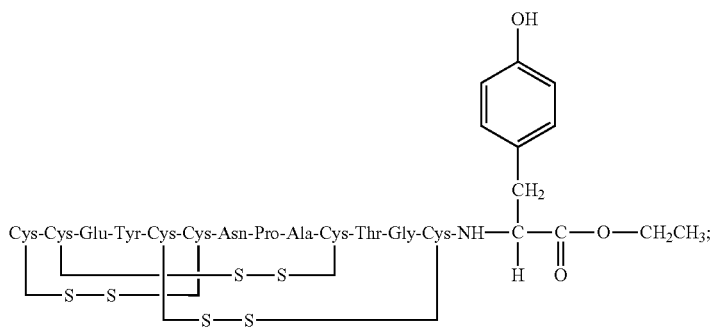

wherein the peptide or pharmaceutically acceptable salt thereof comprises up to 10%, 20%, 30%, 40%, 50%, 60%, 70%, 80%, or 90% by weight compared to the weight of linaclotide.

In further embodiments, the linaclotide composition comprises linaclotide and a peptide or a pharmaceutically acceptable salt thereof, wherein the peptide comprises an amino acid structure of (SEQ ID NO: 13):

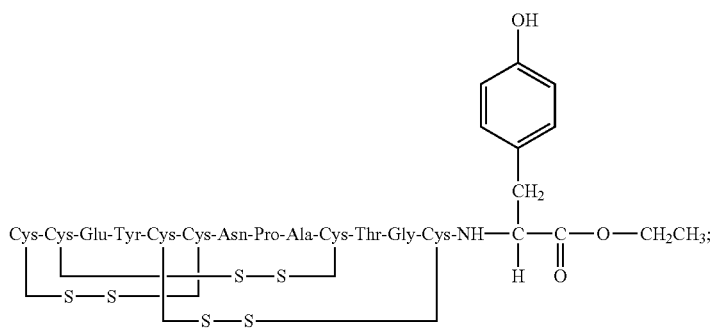

wherein the peptide or pharmaceutically acceptable salt thereof comprises up to 9%, 8%, 7%, 6%, 5%, 4%, 3%, 2%, or 1% by weight compared to the weight of linaclotide.

In some embodiments, the Tyr$_{14}$-ethyl ester peptide comprises up to about 15% by weight of the linaclotide composition, up to about 10% by weight of the linaclotide composition, up to about 7% by weight of the linaclotide composition or up to about 5% by weight of the linaclotide composition. In other exemplary embodiments, the Tyr$_{14}$-ethyl ester comprises from about 0.01% to about 15% by weight of the linaclotide composition, about 0.05% to about 10% by weight of the linaclotide composition, about 0.05% to about 7% by weight of the linaclotide composition or about 0.05% to about 5% by weight of the linaclotide composition.

In other embodiments, the linaclotide composition comprising linaclotide and a peptide or a pharmaceutically acceptable salt thereof, wherein the peptide comprises an amino acid structure of (SEQ ID NO: 10):

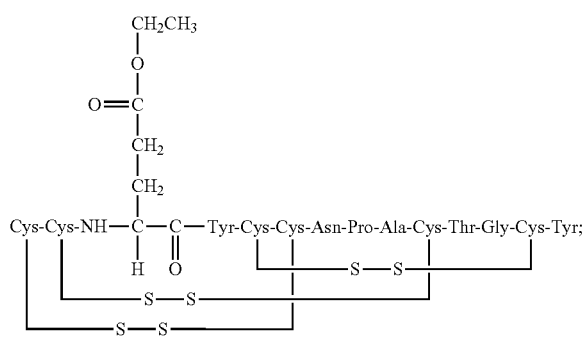

wherein the peptide or pharmaceutically acceptable salt thereof comprises up to 10%, 20%, 30%, 40%, 50%, 60%, 70%, 80%, or 90% by weight compared to the weight of linaclotide.

In further embodiments, the linaclotide composition comprises linaclotide and a peptide or a pharmaceutically acceptable salt thereof, wherein the peptide comprises an amino acid structure of (SEQ ID NO: 10):

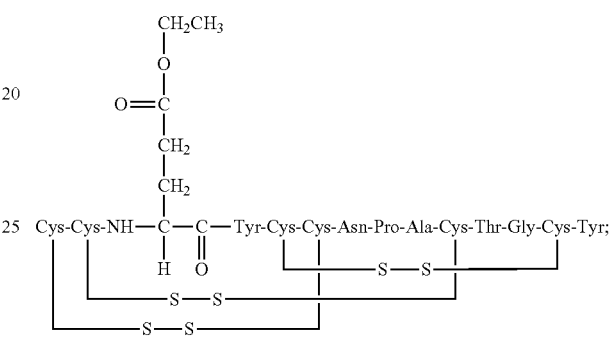

wherein the peptide or pharmaceutically acceptable salt thereof comprises up to 9%, 8%, 7%, 6%, 5%, 4%, 3%, 2%, or 1% by weight compared to the weight of linaclotide.

In some embodiments, the Glu$_3$-ethyl ester peptide comprises up to about 15% by weight of the linaclotide composition, up to about 10% by weight of the linaclotide composition, up to about 7% by weight of the linaclotide composition or up to about 5% by weight of the linaclotide composition. In other exemplary embodiments, the Glu$_3$-ethyl ester comprises from about 0.01% to about 15% by weight of the linaclotide composition, about 0.05% to about 10% by weight of the linaclotide composition, about 0.05% to about 7% by weight of the linaclotide composition or about 0.05% to about 5% by weight of the linaclotide composition.

In some embodiments, the linaclotide composition comprises a peptide or pharmaceutically acceptable salt, wherein the peptide consists of the amino acid structure of (SEQ ID NO: 3):

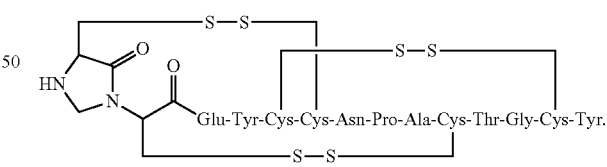

In other embodiments, the linaclotide composition consists essentially of a peptide or pharmaceutically acceptable salt thereof, wherein the peptide comprises the amino acid structure of (SEQ ID NO: 3):

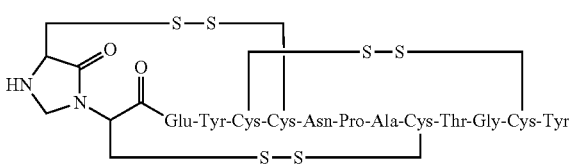

In other embodiments, the linaclotide composition consists linaclotide, a sterically hindered primary amine, a divalent metal cation, a formaldehyde scavenger compound, and one or more of the peptides having the structures of formula (VI) and (VII) or pharmaceutically acceptable salt(s) thereof, wherein the linaclotide composition contains a total combined amount of the peptides of formula (VI) and (VII) up to 3%, 2%, 1%, 0.75%, 0.5%, 0.4%, 0.3%, 0.2%, 0.1%, 0.075%, 0.05%, or even up to 0.01% by weight as compared to the weight of linaclotide.

In other embodiments, the linaclotide composition consists linaclotide, a sterically hindered primary amine, a divalent metal cation, a formaldehyde scavenger compound, and a peptide having the structure of formula (IX) or a pharmaceutically acceptable salt thereof (SEQ ID NO: 20):

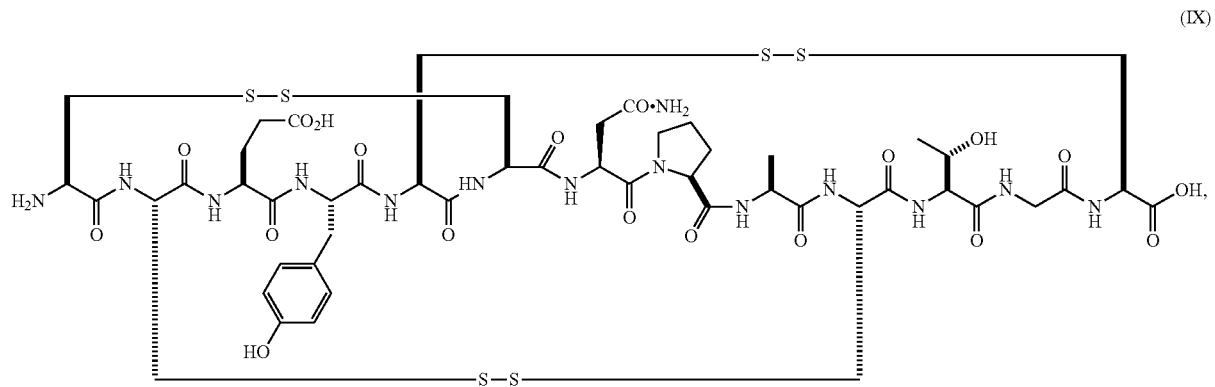

(IX)

wherein the linaclotide composition contains up to 3%, 2%, 1%, 0.75%, 0.5%, 0.4%, 0.3%, 0.2%, 0.1%, 0.075%, 0.05%, or even up to 0.01% by weight of the peptide of formula (IX) as compared to the weight of linaclotide.

In other embodiments, the linaclotide composition consists linaclotide, a sterically hindered primary amine, a divalent metal cation, a formaldehyde scavenger compound, and a peptide having the structure of formula (X) or a pharmaceutically acceptable salt thereof (SEQ ID NO: 21):

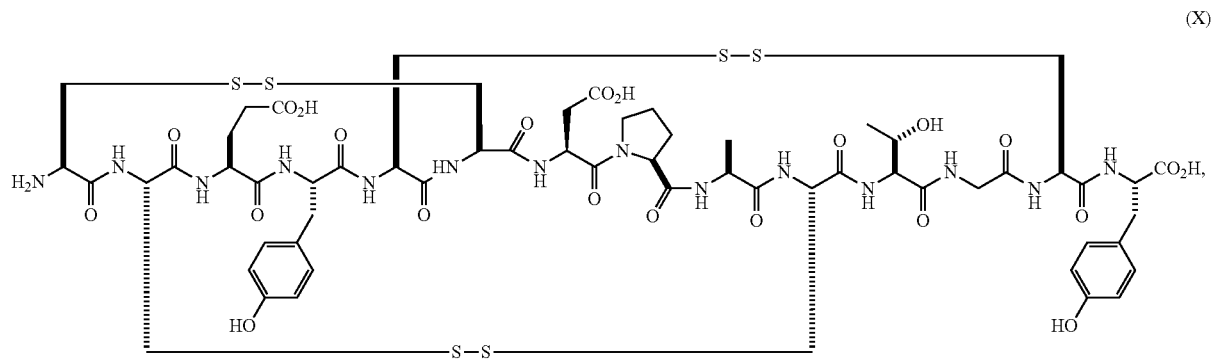

(X)

wherein the linaclotide composition contains up to 3%, 2%, 1%, 0.75%, 0.5%, 0.4%, 0.3%, 0.2%, 0.1%, 0.075%, 0.05%, or even up to 0.01% by weight of the peptide of formula (X) as compared to the weight of linaclotide.

In other embodiments, the linaclotide composition consists linaclotide, a sterically hindered primary amine, a divalent metal cation, a formaldehyde scavenger compound, and a peptide having the structure of formula (XI) or a pharmaceutically acceptable salt thereof (SEQ ID NO: 22):

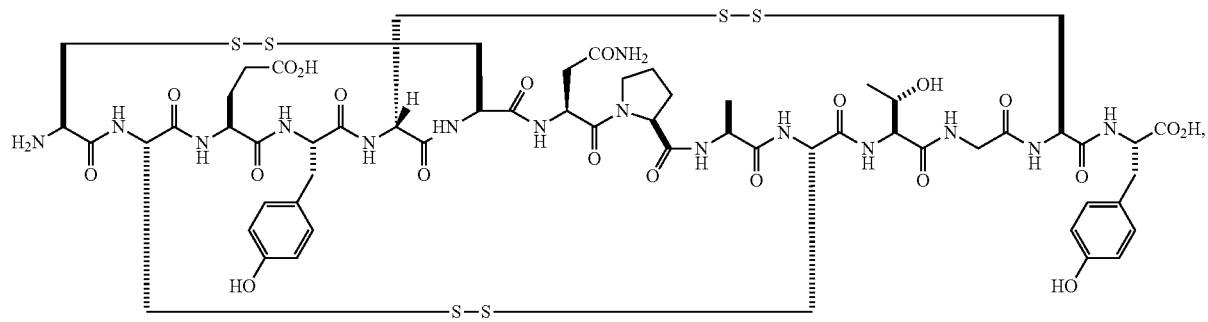

(XI)

wherein the linaclotide composition contains up to 3%, 2%, 1%, 0.75%, 0.5%, 0.4%, 0.3%, 0.2%, 0.1%, 0.075%, 0.05%, or even up to 0.01% by weight of the peptide of formula (XI) as compared to the weight of linaclotide.

In other embodiments, the linaclotide composition consists linaclotide, a sterically hindered primary amine, a divalent metal cation, a formaldehyde scavenger compound, and a peptide having the structure of formula (XII) or a pharmaceutically acceptable salt thereof (SEQ ID NO: 23):

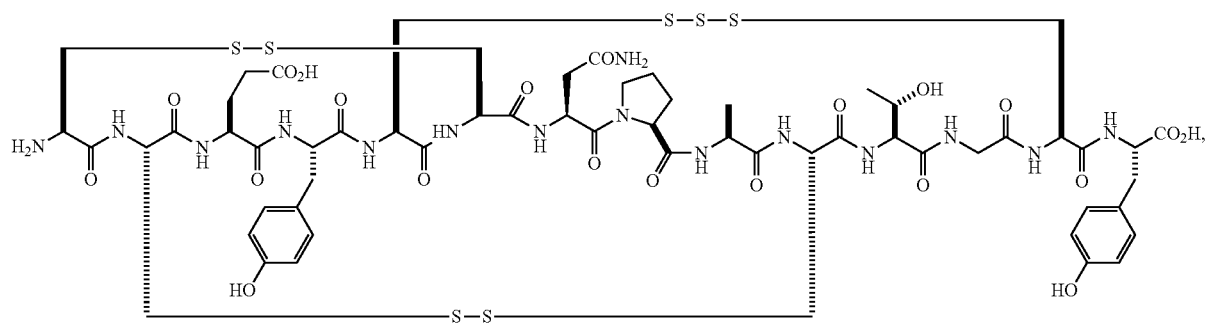

(XII)

wherein the linaclotide composition contains up to 3%, 2%, 1%, 0.75%, 0.5%, 0.4%, 0.3%, 0.2%, 0.1%, 0.075%, 0.05%, or even up to 0.01% by weight of the peptide of formula (XII) as compared to the weight of linaclotide.

In other embodiments, the linaclotide composition consists linaclotide, a sterically hindered primary amine, a divalent metal cation, a formaldehyde scavenger compound, and a peptide having the structure of formula (XIII) or a pharmaceutically acceptable salt thereof (SEQ ID NO: 24):

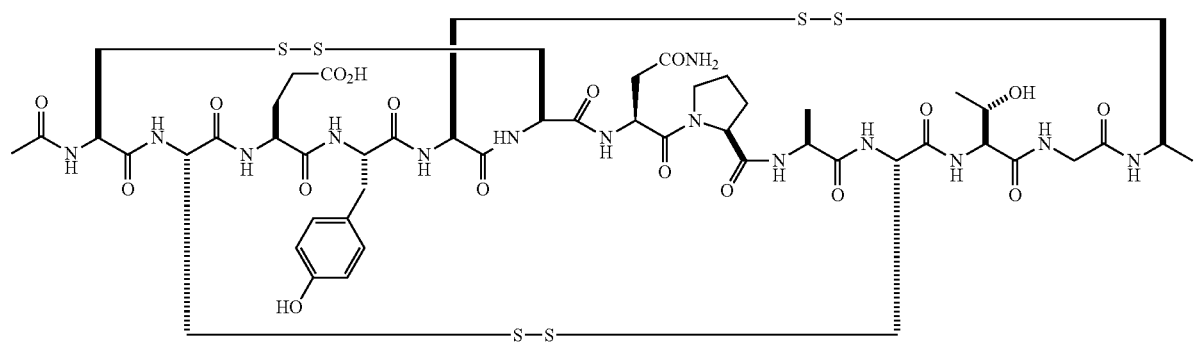

(XIII)

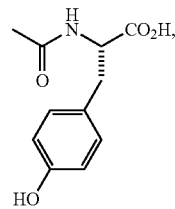

wherein the linaclotide composition contains up to 3%, 2%, 1%, 0.75%, 0.5%, 0.4%, 0.3%, 0.2%, 0.1%, 0.075%, 0.05%, or even up to 0.01% by weight of the peptide of formula (XIII) as compared to the weight of linaclotide.

In other embodiments, the linaclotide composition consists linaclotide, a sterically hindered primary amine, a divalent metal cation, a formaldehyde scavenger compound, and a peptide having the structure of formula (XIV) or a pharmaceutically acceptable salt thereof (SEQ ID NO:10):

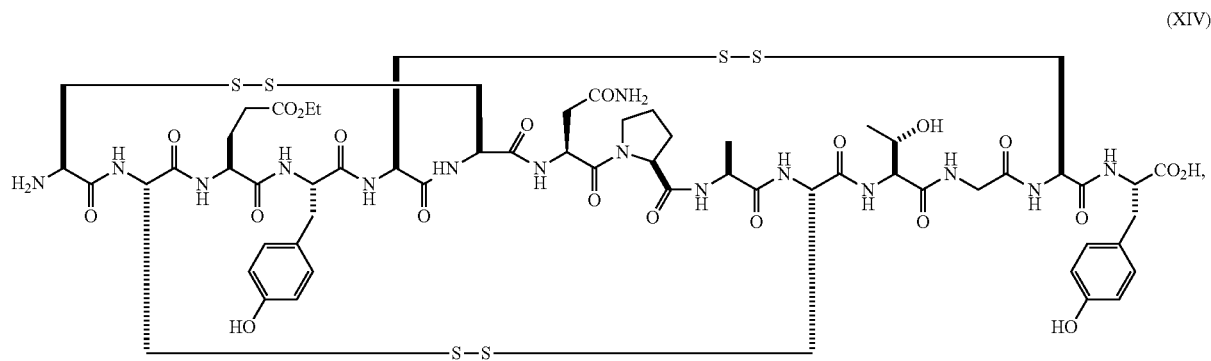

(XIV)

wherein the linaclotide composition contains up to 3%, 2%, 1%, 0.75%, 0.5%, 0.4%, 0.3%, 0.2%, 0.1%, 0.075%, 0.05%, or even up to 0.01% by weight of the peptide of formula (XIV) as compared to the weight of linaclotide.

In other embodiments, the linaclotide composition consists linaclotide, a sterically hindered primary amine, a divalent metal cation, a formaldehyde scavenger compound, and a peptide having the structure of formula (XV) or a pharmaceutically acceptable salt thereof (SEQ ID NO: 13):

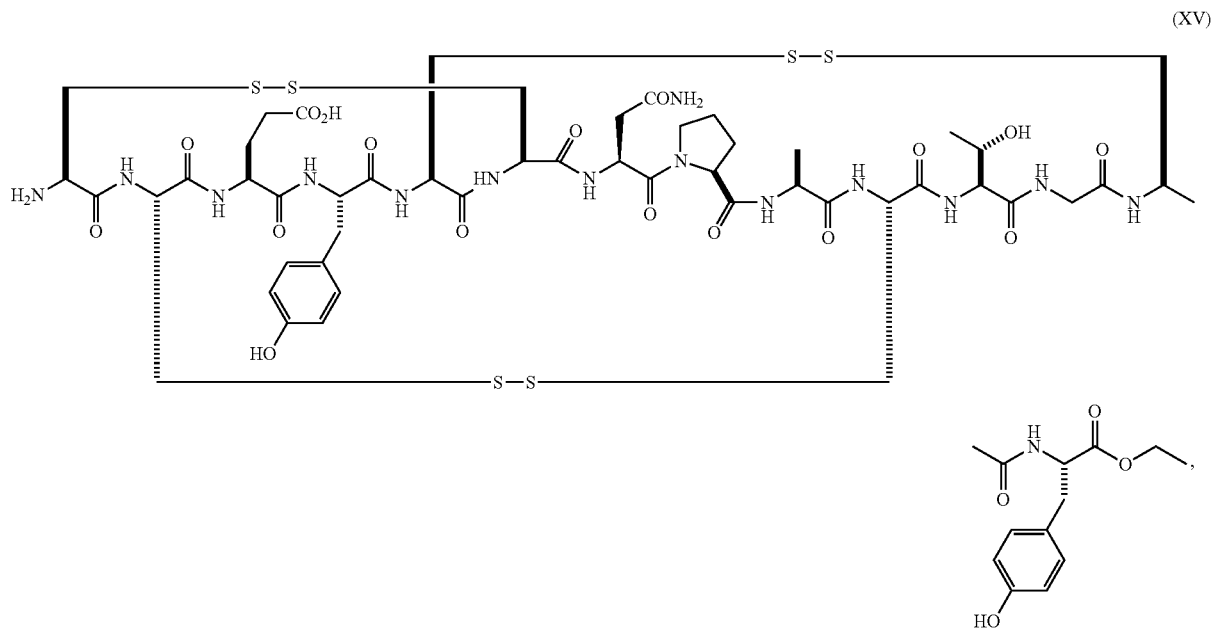

(XV)

wherein the linaclotide composition contains up to 3%, 2%, 1%, 0.75%, 0.5%, 0.4%, 0.3%, 0.2%, 0.1%, 0.075%, 0.05%, or even up to 0.01% by weight of the peptide of formula (XV) as compared to the weight of linaclotide.

Methods of Treatment

In various embodiments, a patient diagnosed with a gastrointestinal disorder is provided with the linaclotide composition described herein, wherein the gastrointestinal disorder is selected from the group consisting of irritable bowel syndrome (IBS) (such as constipation-predominant IBS), constipation (such as chronic idiopathic constipation), a functional gastrointestinal disorder, gastroesophageal reflux disease, functional heartburn, dyspepsia, visceral pain, gastroparesis, chronic intestinal pseudo-obstruction, colonic pseudo-obstruction, Crohn's disease, ulcerative colitis, and inflammatory bowel disease.

In a further embodiment, the gastrointestinal disorder is constipation. The constipation can be chronic idiopathic constipation, idiopathic constipation, due to post-operative ileus, or caused by opiate use. Clinically accepted criteria that define constipation include the frequency of bowel movements, the consistency of feces and the ease of bowel movement. One common definition of constipation is less than three bowel movements per week. Other definitions include abnormally hard stools or defecation that requires excessive straining (Schiller 2001, Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple Sclerosis, Parkinson's disease, spinal cord lesions, Neurofibromatosis, autonomic neuropathy, Chagas disease, Hirschsprung's disease and Cystic fibrosis. Constipation may also be the result of surgery (postoperative ileus) or due to the use of drugs such as analgesics (like opioids), antihypertensives, anticonvulsants, antidepressants, antispasmodics and antipsychotics.

In other embodiments, the gastrointestinal disorder is irritable bowel syndrome (IBS). The irritable bowel syndrome can be constipation-predominant irritable bowel syndrome (c-IBS), diarrhea-predominant irritable bowel syndrome (d-IBS) or alternating between the two irritable bowel syndromes (a-IBS).

In other embodiments, the gastrointestinal disorder is dyspepsia.

In other embodiments, the gastrointestinal disorder is gastroparesis. The gastroparesis can be selected from idiopathic, diabetic or post-surgical gastroparesis.

In still other embodiments, the gastrointestinal disorder is chronic intestinal pseudo obstruction.

In other embodiments, the gastrointestinal disorder is Crohn's disease.

In some embodiments, the gastrointestinal disorder is ulcerative colitis.

In some embodiments, the gastrointestinal disorder is inflammatory bowel disease.

In still another embodiment, the invention features a method for treating a gastrointestinal disorder comprising providing a patient diagnosed with IBS-C or CC with the linaclotide composition described herein.

It has been discovered in some embodiments, that linaclotide is only to be administered to patients without known or suspected mechanical gastrointestinal obstruction. In this regard, prior to administering or providing the linaclotide composition to patients diagnosied with a GI disorder, the patient is evaluated for symptoms suggestive of mechanical gastrointestinal obstruction prior to initiating treatment.

Moreover, in some embodiments, the linaclotide composition is provided to patients diagnosed with a GI disorder and not currently or frequently experiencing diarrhea.

In some embodiments, the method comprises after administering or providing the linaclotide composition to a patient, monitoring the patient for diarrhea, flatulence, abdominal pain, abdominal distension, Defecation urgency, dyspepsia, gastroesophageal reflux disease, upper abdominal pain, vomiting; viral gastroenteritis; muscle strain; dizziness; sinus congestion, fecal incontinence, dehydration and/or headache, and optionally decreasing the linaclotide dose administered to patients experiencing one or more of these adverse reactions to the initial dosage.

In some embodiments, the method comprises after administering or providing the linaclotide composition to a patient, periodically assess the need for continued treatment with linaclotide.

In some embodiments, the method comprises after administering or providing the linaclotide composition to a patient, determining that the patient receiving the linaclotide composition is experiencing severe or intolerable diarrhea, and reducing the linaclotide dose or suspending treatment.

In some embodiments, the method comprises diagnosing the patient with IBS-C or CC, administering or providing the linaclotide composition to the patient and counseling the patient that improvement of bowel symptoms should occur within the first week of treatment, but improvement of abdominal symptoms may take longer.

In some embodiments, the method comprises periodically assessing the need for continued treatment with the linaclotide composition.

In this regard, the efficacy of oral dosage forms comprising 290 mg for the management of IBS-C was established in two double-blind, placebo-controlled, randomized, multicenter studies in adult patients. A total of 800 patients in Study 1 and 804 patients in Study 2 (overall mean age of 43.9 years [range 18-87 years with 5.3% ≥65 years of age], 90.1% female, 77.4% white, 18.8% black, and 12.0% Hispanic) received treatment with LINZESS 290 mcg or placebo once daily and were evaluated for efficacy. All patients met Rome II criteria for IBS and were required to report a mean abdominal pain score of ≥3 on a 0-to-10-point numeric rating scale, <3 complete spontaneous bowel movements (CSBMs; a CSBM is a spontaneous bowel movement [SBM] that is associated with a sense of complete evacuation; an SBM is a bowel movement occurring in the absence of laxative use), and ≤5 SBMs per week during a 2-week baseline period. The study designs were identical through the first 12 weeks, and thereafter differed only in that Study 1 included a 4-week randomized withdrawal (RW) period, and Study 2 continued for 14 additional weeks (total of 26 weeks) of double-blinded treatment.

Efficacy of the oral dosage form of linaclotide was assessed using responder and change-from-baseline endpoints. Results for endpoints were based on information provided daily by patients. An abdominal pain responder was a patient who had ≥30% reduction in mean abdominal pain from baseline in a given week for ≥6 out of 12 weeks of the treatment period. A CSBM responder was a patient who had an increase of ≥1 CSBM from baseline in a given week for ≥6 out of 12 weeks of the treatment period. To be a combined responder, a patient had to meet both abdominal pain and CSBM weekly responder criteria in the same week for ≥6 out of 12 weeks of the treatment period. The efficacy results are shown in Table 2. In both studies, the proportion of patients who were responders to the oral dosage form of 290 mcg linaclotide was statistically significantly higher than with placebo.

For change-from-baseline endpoints, patients who received the oral dosage form of 290 mcg linaclotide across the 2 studies had statistically significantly (p<0.0001) greater improvements compared with patients receiving placebo in abdominal symptoms, including abdominal pain, abdominal discomfort, and bloating; and bowel function, including stool frequency (CSBM and SBM) and consistency (i.e., hardness of stool), as well as straining. Sixty-seven percent of the patients had an SBM within 24 hours of taking their first dose versus 42% of placebo patients (p<0.0001).

The proportions of patients who met response criteria of increasing levels of symptom improvement compared to baseline (i.e., decreases of >0%, ≥10%, ≥20%, ≥30%, ≥40%, ≥50%, and ≥60% in abdominal pain and increases of >0, ≥1, ≥2, ≥3, ≥4, ≥5, and ≥6 CSBMs per week) over 12 weeks of treatment were analyzed. At each level, a statistically significantly greater proportion of patients treated with the oral dosage form of 290 mcg linaclotide met the response criterion compared to placebo patients. Moreover, the oral dosage form of 290 mcg linaclotide demonstrated a statistically significant separation from placebo that was present at the first week and sustained across the 26 weeks of the treatment period (p<0.001 at all time points during the treatment period). Similar results for improvement in CSBM frequency were demonstrated throughout the 26-week treatment period. Maximum effect on CSBM frequency occurred by Week 1, but the effect on abdominal pain continued to increase over the first 6 to 8 weeks. During the 4-week RW period in Study 2 when treatment with the oral dosage form of 290 mcg linaclotide was discontinued, bowel symptoms returned toward baseline within the first week with no evidence of rebound worsening compared to baseline; abdominal symptoms also returned toward baseline with no evidence of rebound.

The efficacy of the oral dosage form of 290 mcg linaclotide for the management of CC was established in two double-blind, placebo-controlled, randomized, multicenter studies in adult patients. A total of 642 patients in Study 3 and 630 patients in Study 4 (overall mean age of 47.8 years [range 18-85 years with 12.1% ≥65 years of age], 88.9% female, 76.2% white, 21.5% black, Hispanic 10.0%) received treatment with the oral dosage form of 145 or 290 mcg linaclotide, or placebo once daily and were evaluated for efficacy. All patients met Rome II criteria for CC and were required to report <3 CSBMs and ≤6 SBMs per week during a 2-week baseline period. Patients were excluded if they met criteria for IBS. The study designs differed only in that Study 3 had a 4-week RW period following the 12-week treatment period.

Efficacy of the oral dosage form of 145 or 290 mcg linaclotide was assessed using responder and change-from-baseline endpoints. Results for endpoints were based on information provided daily by patients. A CSBM responder was defined differently in the CC studies than it was in the IBS-C studies. A CSBM responder in the CC studies was a patient who had ≥3 CSBMs and an increase of ≥1 CSBM from baseline in a given week for ≥9 out 12 weeks of the treatment period. both studies, the proportion of patients who were CSBM responders was statistically significantly greater with each dose of LINZESS (145 and 290 mcg) than with placebo.

For change-from-baseline endpoints, patients who received either dose of the oral dosage form of linaclotide across the 2 studies had statistically significantly (p<0.0001) greater improvements compared with patients receiving placebo in abdominal discomfort, bloating, stool frequency (CSBM and SBM), stool consistency (i.e., hardness of stool), and straining. Sixty-seven percent and 57% of linaclotide 145 and 290 mcg patients, respectively, had an SBM within 24 hours of taking their first dose versus 39% of placebo patients (p<0.0001 for both doses versus placebo).

The proportions of patients who met response criteria of increasing levels of stool frequency compared to baseline (i.e., increases of >0, ≥1, ≥2, ≥3, ≥4, ≥5 and ≥6 CSBMs per week) over 12 weeks of treatment were analyzed. At each level, a statistically significantly greater proportion of patients treated with either dose of the oral dosage form of linaclotide met the response criterion compared with placebo patients.

For CSBM and SBM frequency, each dose of LINZESS (145 and 290 mcg) demonstrated a statistically significant separation from placebo that was present at the first week and sustained across the 12 weeks of the treatment period (p<0.001 for each dose vs. placebo at all time points). During the 4-week RW period in Study 3 when LINZESS treatment was discontinued, bowel function, including CSBMs and SBMs, returned toward baseline within the first week with no evidence of rebound worsening (see FIG. 3).

In some preferred embodiments, the linaclotide composition is stored up to 25° C. (77° F.); excursions permitted between 15° C. and 30° C. (59° F. and 86° F.) [see USP Controlled Room Temperature]. In some embodiments, the linaclotide composition is stored is a low moisture environment.

As used herein, unless otherwise indicated, the phrase "consisting of" when used in reference to the linaclotide composition or a single component of the composition means that the linaclotide composition or single component defined by the phrase contains no other components than those specified but may contain additional components that are unrelated to the invention and/or impurities ordinarily associated with the recited steps or components.

Dosage and Excipients

The linaclotide composition may any suitable oral pharmaceutical dosage form (e.g., capsules) containing any suitable therapeutic dosage of linaclotide. In some embodiments, the linaclotide composition comprises capsules/tablets that comprise 290 mcg which are to be taken orally once daily on an empty stomach, such as for treating IBS-c (IBS with constipation. In some embodiments, the linaclotide composition comprises capsules/tablets that comprise 145 or 290 mcg which are to be taken orally once daily on an empty stomach for treating chronic idiopathic constipation.

The linaclotide composition can include additional ingredients or excipient. In certain embodiments, one or more therapeutic agents of the dosage unit may exist in an extended or control release formulation and additional therapeutic agents may not exist in extended release formulation. For example, a peptide or agonist described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents.

The linaclotide composition can comprise any pharmaceutically tolerable carrier or medium, e.g. solvents, dispersants, coatings, absorption promoting agents, controlled release agents, and one or more inert excipients (which include starches, polyols, granulating agents, microcrystalline cellulose (e.g. celphere, Celphere Beads®), diluents, lubricants, binders, disintegrating agents, and the like), etc. If desired, tablet dosages of the disclosed compositions may be coated by standard aqueous or nonaqueous techniques.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, microcrystalline cellulose (e.g. AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30), and mixtures thereof.

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating the peptides include, without limitation, talc, microcrystalline cellulose (e.g., Avicel PH101 or Celphere CP-305), powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes. As used herein, an "excipient" is any pharmaceutically acceptable additive, filler, binder or agent.

The linaclotide composition may also optionally include other therapeutic ingredients, anti-caking agents, preservatives, sweetening agents, colorants, flavors, desiccants, plasticizers, dyes, glidants, anti-adherents, anti-static agents, surfactants (wetting agents), anti-oxidants, film-coating agents, and the like. Any such optional ingredient must be compatible with the compound described herein to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The linaclotide composition can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or non-aqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the peptides compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable antioxidants include, for example, BHA (butylated hydroxyanisole), BHT (butylated hydroxytoluene), vitamin E, propyl gallate, ascorbic acid and salts or esters thereof, tocopherol and esters thereof, alpha-lipoic acid and beta-carotene.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoat (e.g. Aquacoat Ethylcellulose Aqueous Dispersion, 15% w/w, FMC Biopolymer, ECD-30), Eudragit (e.g. Eudragit E PO PE-EL, Roehm Pharma Polymers) and Opadry (e.g Opadry AMB dispersion, 20% w/w, Colorcon).

In certain embodiments, suitable additives for the peptides composition include one or more of sucrose, talc, magnesium stearate, crospovidone or BHA.

The compositions of the present invention can also include other excipients, agents, and categories thereof including but not limited to L-histidine, Pluronic®, Poloxamers (such as Lutrol® and Poloxamer 188), ascorbic acid, glutathione, permeability enhancers (e.g. lipids, sodium cholate, acylcarnitine, salicylates, mixed bile salts, fatty acid micelles, chelators, fatty acid, surfactants, medium chain glycerides), protease inhibitors (e.g. soybean trypsin inhibitor, organic acids), pH lowering agents and absorption enhancers effective to promote bioavailability (including but not limited to those described in U.S. Pat. No. 6,086,918 and U.S. Pat. No. 5,912,014), materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD& C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments, there is provided a pharmaceutical composition comprising a peptide described herein and one or more agents selected from $Mg^{2+}$, $Ca^{2+}$, $Zn^{2+}$, $Mn^{2+}$, $K^+$, $Na^+$ or $Al^{3+}$, a combination thereof, and/or a sterically hindered primary amine. In further embodiments, the agent is $Mg^{2+}$, $Ca^{2+}$ or $Zn^{2+}$ or a combination thereof. In some embodiments, the divalent metal cation is provided, without limitation, as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride.

In other embodiments, the cation is provided as calcium chloride, magnesium chloride or zinc acetate.

In another embodiment, the agent is a sterically hindered primary amine. In a further embodiment, the sterically hindered primary amine is an amino acid. In yet a further embodiment, the amino acid is a naturally-occurring amino acid. In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, glycine and valine; yet further, the naturally-occurring amino acid is leucine, isoleucine, alanine or methionine. In a still further embodiment, the naturally-occurring amino acid is leucine. In another embodiment, the sterically hindered primary amine is a non-naturally occurring amino acid (e.g., 1-aminocyclohexane carboxylic acid). In a further embodiment, the sterically hindered primary amine is cyclohexylamine, 2-methylbutylamine or chitosan. In another embodiment, one or more sterically hindered primary amines may be used in a composition.

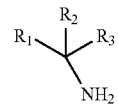

In some cases, the sterically hindered primary amine has the formula: wherein $R_1$, $R_2$ and $R_3$ are independently selected from: H, C(O)OH, C1-C6 alkyl, C1-C6 alkylether, C1-C6 alkylthioether, C1-C6 alkyl carboxylic acid, C1-C6 alkyl carboxylamide and alkylaryl, wherein any group can be singly or multiply substituted with: halogen or amino, and provided that no more than two of $R_1$, $R_2$ and $R_3$ are H. In another embodiment, no more than one of $R_1$, $R_2$ and $R_3$ is H.

In other embodiments, there is provided a pharmaceutical composition comprising a pharmaceutically acceptable carrier, peptide, a cation selected from $Mg^{2+}$, $Ca^{2+}$, $Zn^{2+}$, $Mn^{2+}$, $K^+$, $Na^+$ or $Al^{3+}$, or a mixture thereof, and a sterically hindered primary amine. In one embodiment, the cation is $Mg^{2+}$, $Ca^{2+}$ or $Zn^{2+}$ or a mixture thereof. In a further embodiment, the linaclotide composition further comprises a pharmaceutically acceptable binder and/or a pharmaceutically acceptable glidant, lubricant or additive that acts as both a glidant and lubricant and/or an antioxidant. In some embodiments, the linaclotide composition is applied to a carrier. In some embodiments, the carrier is a filler.

In some cases the molar ratio of cation:sterically hindered primary amine:peptide in the aqueous solution applied to the carrier is 5-100:5-50:1. In some cases, the molar ratio of cation:sterically hindered primary amine may be equal to or greater than 2:1 (e.g., between 5:1 and 2:1). Thus, in some cases the molar ratio of cation:sterically hindered primary amine:peptide applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. In some preferred embodiments, the molar ratio of divalent metal cation: sterically hindered primary amine:linaclotide is about 57-63: 28-32:1. When binder, e.g., methylcellulose, is present in the GC-C agonist peptide solution applied to the carrier it can be present at 0.5%-2.5% by weight (e.g., 0.7%-1.7% or 0.7%-1% or 1.5% or 0.7%).

In a further embodiment, the linaclotide composition further comprises a pharmaceutically acceptable binder or additive, and/or a pharmaceutically acceptable glidant, lubricant or additive that acts as both a glidant and lubricant and/or an antioxidant.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

As used herein, unless otherwise indicated, the phrase "consisting essentially of," when used in reference to the linaclotide composition or a single component of the composition means that the composition or single component defined by the phrase contains no active pharmaceutical ingredients other than those specified but that it may contain any additional inactive components or excipients or formaldehyde scavenger compound(s).

The term "linaclotide composition" is used herein, unless otherwise indicated, to mean a composition that comprises linaclotide, excipients necessary for stabilizing, storing and delivering linaclotide as described herein (e.g., a divalent metal cation and an amino acid, for example, in a molar ratio of divalent metal cation:amino acid:linaclotide of about 57-63:28-32:1) and optionally one or more formaldehyde scavenger compounds in any suitable configuration or conformation. For example, in some embodiments, the linaclotide composition comprises an oral pharmaceutical dosage form (e.g., capsules or tablets) that comprises linaclotide (in any desired dosage, such as 145 μg or 290 μg), excipients necessary for stabilizing, storing and delivering linaclotide as described herein (e.g., a divalent metal cation and an amino acid for example in a molar ratio of divalent metal cation:amino acid:linaclotide of about 57-63:28-32:1) and one or more formaldehyde scavenger compounds. In other preferred embodiments, the linaclotide composition comprises an oral pharmaceutical dosage form (e.g., capsules or tablets) that comprises linaclotide (in any desired dosage, such as 145 μg or 290 μg) and excipients necessary for stabilizing, storing and delivering linaclotide such as described herein (e.g., a divalent metal cation and an amino acid in a molar ratio of divalent metal cation:amino acid:linaclotide of about 57-63:28-32:1) and one or more separate formaldehyde scavenger compounds that are outside of the oral dosage form (e.g., but in the same bottle, canister, or container).

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

EXAMPLES

The GC-C agonist peptides or pharmaceutically acceptable salts thereof as described herein were prepared by solid phase chemical synthesis and natural folding (air oxidation) by American Peptide Company (Sunnyvale, Calif.). In some cases, the peptides were modified after synthesis as described herein.

The $Cys_1$-IMD (SEQ ID NO: 3) peptide was synthesized by mixing 4.6 g (3.0 mmol) of linaclotide in 200 ml of EtOH. Formaldehyde at 37% (1.12 ml/5 eq) was added to this mixture. The reaction mixture was incubated in a water bath (45 □C) for overnight. The following day the solvent was removed by rota-evaporation. The peptide was further purified through reverse-phase chromatography.

The $Glu_3$-ethyl ester (SEQ ID NO: 10) peptide was synthesized on a 20 mmol Fmoc-Tyr(tBu)-Wang resin. Protecting groups used for amino acids are: t-Butyl group for Tyr and Thr, Trt group for Asn and Cys. The peptide chain was assembled on the resin by repetitive removal of the Fmoc protecting group and coupling of protected amino acid. DIC and HOBt were used as coupling reagents and NMM was used as the base for this reaction. 20% piperidine in DMF was used as de-Fmoc-reagent. After removal of last Fmoc protecting group, resin was treated with cocktail K for 3 hours to cleave the peptide from resin and removal of the side chain protecting groups. The eluted peptide was precipitated in cold ether and dried. The dried peptide was dissolved in a mixture of TFA/TIS/water (95:3:2v/v) in a ratio of 1 to 10 (g/v). This mixture was stirred at room temperature for 1 hour. The isolated peptide was also precipitated in cold ether, collected by filtration and dried under high vacuum.

The $Tyr_{14}$-ethyl ester (SEQ ID NO: 13) peptide was synthesized by a fragment condensation method. Fragment A (Boc-Cys(Trt)-Cys(Trt)-Glu(OtBu)-Tyr(tBu)-Cys(Trt)-Cys(Trt)-Asn(Trt)-Pro-Ala-Cys(Trt)-Thr(tBu)-Gly-OH) was prepared on 15 mmol CTC resin using Fmoc chemistry. This peptide chain was also assembled on the resin by repetitive removal of the Fmoc protecting group and coupling of protected amino acid. DIC and HOBt were used as coupling reagents and NMM was used as the base. 20% piperidine in DMF was used as de-Fmoc-reagent. After removal of last Fmoc protecting group, Boc was coupled to protect the N-terminal amino group. The peptide resin was washed, dried, and treated with 1% TFA/DCM to cleave peptide from resin. Fragment B (Cys(Trt)-Tyr-OEt) was prepared from coupling of Fmoc-Cys(Trt)-OH and Tyr-OEt. HCl. The Fmoc group was removed by treating this di-peptide with 20% piperidine in DMF.

The $Tyr_{14}$-ethyl ester peptide was finally synthesized by coupling the two fragments in DMF. HBTU/HOBt/NMM was used as the coupling reagent for this reaction. The protecting groups were removed by treating the peptide with cocktail K for 2 hours. This peptide was precipitated in cold ether and dried. The dried peptide was dissolved in a mixture of TFA/TIS/water (95:3:2v/v) in a ratio of 1 to 10 (g/v). This mixture was stirred at room temperature for 1 hour. The isolated peptide was again precipitated in cold ether, collected by filtration and dried under high vacuum.

Example 1 cGMP Accumulation in T84 Cells for Analysis of GC-C Activity

For the cGMP assay, $4.5 \times 10^5$ cells/mL of T84 cells were grown overnight in 24 well tissue culture plates. On next day, the T84 cells were washed twice with 1 mL of DMEM (pH 7). After the second wash, the cells were incubated with 450 μL of 1 mM isobutylmethylxanthine (IBMX) in pH 7 buffer for 10 minutes at 37° C. to inhibit any phosphodiesterase activity. The peptides were then diluted in DMEM buffer (pH 7) to a 10× concentration. The peptide solution of 50 μL was diluted to a final volume of 500 μL with the T84 cells, bringing each peptide concentration to 1×. The peptides were tested in duplicate at 100 nM.

There was no peptide control used to determine endogenous levels of cGMP. Peptides were incubated for 30 minutes at 37° C. After 30 minutes, the supernatants were removed and the cells were lysed with 0.1 M HCl. The cells were lysed for 30 minutes on ice. After 30 minutes, lysates were pipetted off and placed into a 96 well HPLC plate and spun at 10,000×G for 10 minutes to remove any cell debris. Supernatants from the previous spin were removed and placed into a fresh 96 well HPLC plate.

cGMP concentrations were determined from each sample using the LC/MS conditions (Table 1 below) and calculated standard curve. $EC_{50}$ values were calculated from concentration-response curves generated with GraphPad Prism Software.

TABLE 1

LC/MS conditions

| | |
|---|---|
| MS: | Thermo Quantum |
| Ion Mode: | ESI$^+$ |
| Scan Type: | MRM |

| Compound: | | | | | |
|---|---|---|---|---|---|
| | Transition | Dwell Time (msec) | Collision Energy (V) | Tube Lens | Retention Time (min) |
| cGMP | 346 > 152 | 100 | 28 | 139 | 1.0 |

| | |
|---|---|
| HPLC: | Agilent Technologies 1200 Series with CTC Analytics HTS PAL |
| Column: | Thermo Hypersil Gold 2.1 × 50 mm 5 micron particle size |
| Flow Rate: | 400 uL/min |
| Column Temperature: | RT |
| Autosampler Temperature: | 6° C. |
| Injection Volume: | 20 uL |
| Mobile Phases: | A = 98:2 Water:Acetonitrile + 0.1% Formic Acid |
| | B = 2:98 Water:Acetonitrile + 0.1% Formic Acid |

| Gradient: | | |
|---|---|---|
| Time (min) | % A | % B |
| 0 | 100 | 0 |
| 0.3 | 30 | 70 |
| 2.00 | 30 | 70 |
| 2.01 | 100 | 0 |
| 4 | 100 | 0 |

Example 2

Relative Binding Affinity of Exemplary Peptides to the GC-C Receptor of T84 Cells The relative binding affinities of linaclotide and $Cys_1$-IMD to the guanylate cyclase-C receptor (GC-C) were determined using a competitive-binding assay in which the peptides competed with a known GC-C agonist, porcine-derived heat-stable enterotoxin (pSTa), for binding sites on cell-surface GC-C receptors on human colonic epithelial (T84) cells. The pSTa was radiolabeled with $^{125}$I to enable measurement of its receptor binding. The competitive-binding assay was performed by adding various concentrations of each peptide (0.1 to 3,000 nM) to 0.20 mL reaction mixtures containing Dulbecco's modified Eagle's medium (DMEM), 0.5% bovine serum albumin (BSA), $2.0×10^5$ T84 cells, and 170 pM [$^{125}$I]-pSTa (200,000 cpm). The data were used to construct competitive radioligand-binding curves and determine the relative binding affinities of linaclotide and $Cys_1$-IMD, as measured by their $IC_{50}$ and $K_i$ values.

Figure 3:
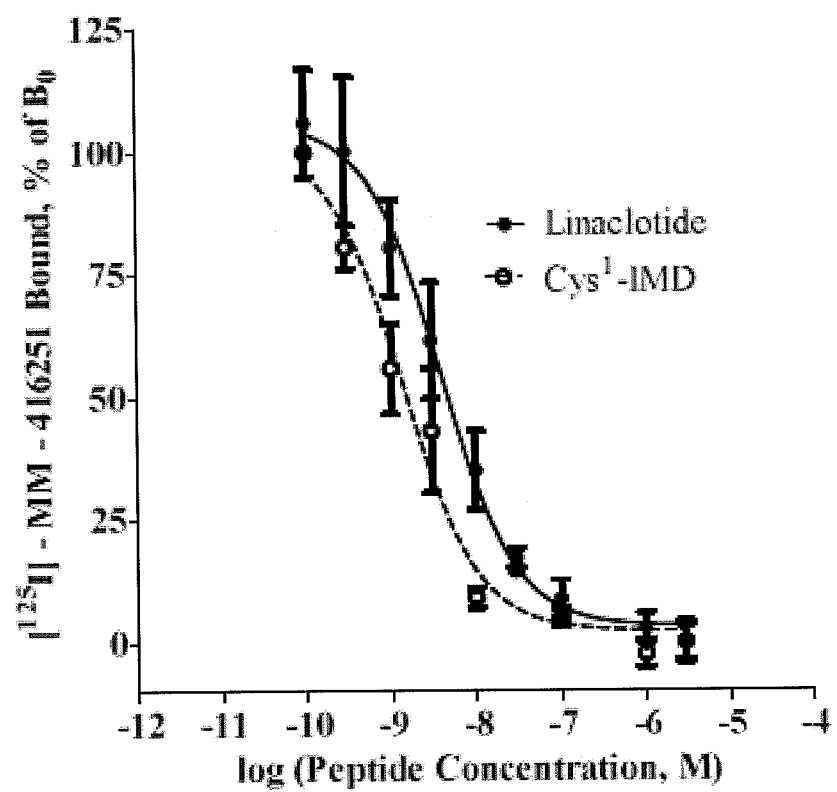
FIG. 3 shows specific binding of linaclotide and $Cys_1$-IMD to cell-surface GC-C receptors on T84 cells in a competitive radioligand binding assay.

Both linaclotide and $Cys_1$-IMD competitively inhibited the specific binding of [$^{125}$I]-pSTa to cell-surface GC-C receptors on T84 cells. Their relative binding affinities, as measured by their inhibition constants ($K_i$), were as follows: Linaclotide $K_i$=3.9±1.6 nM and $Cys_1$-IMD $K_i$=1.4±0.5 nM (FIG. 3).

Example 3 cGMP Response in T84 Cells Induced by Exemplary Peptides

Linaclotide and $Cys_1$-IMD were tested for guanylate cyclase-C (GC-C) agonist activity in T84 cells as follows. In each well of a 96-well plate, approximately 200,000 T84 cells/well was first incubated with 1 mM 3-isobutyl-1-methylxanthine (IBMX) in 0.18 mL of Dulbecco's modified Eagle's medium (DMEM) for 10 minutes at 37° C. Each peptide was diluted to final concentrations ranging from 0.1 to 10,000 nM, and 0.02 mL of each dilution was added in duplicate to a 96-well plate containing the T84 cells, for a final volume of 0.20 mL per well. The peptide reactions were incubated for 30 min at 37° C. Following the incubation, the supernatants were removed and discarded and the cells were lysed with cold 0.1 M hydrochloric acid (HCl) for 30 min on ice. The cell debris was removed by centrifugation and the concentration of guanosine 3',5'-cyclic monophosphate (cyclic GMP) in each lysate was determined using liquid chromatography with tandem mass spectrometry. The data were used to construct dose-response curves and calculate half-maximal effective concentration ($EC_{50}$) values for each test article.

Figure 4:
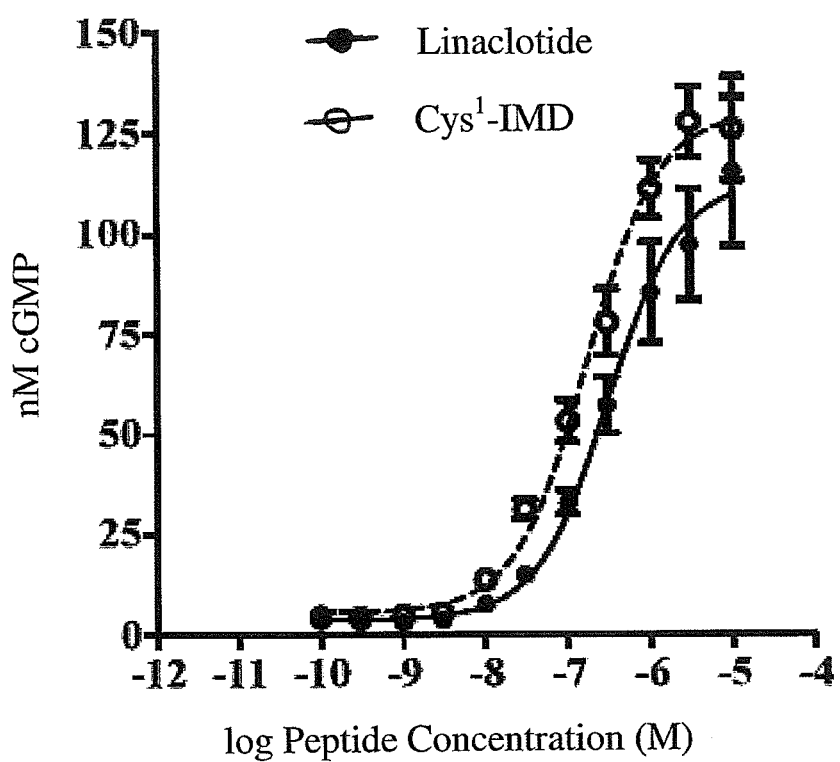
FIG. 4 shows the dose response of exemplary peptides of the present invention in a T84 cell c-GMP assay.

Linaclotide and $Cys_1$-IMD showed GC-C agonist activity in T84 cells, as measured by the increase in intracellular cGMP (FIG. 4). The $EC_{50}$ values for linaclotide and $Cys_1$-IMD were 315±105 nM and 172±32 nM, respectively.

Example 4

Measurement of Content and Purity of Exemplary Peptides

Content and purity of the peptides of the present invention may be determined by reverse phase gradient liquid chromatography using an Agilent Series 1100 LC System with Chemstation Rev A.09.03 software or equivalent. A YMC Pro™ C18 column (dimensions: 3.0×150 mm, 3.5 um, 120 Å; Waters Corp., Milford, Mass.) or equivalent is used and is maintained at 40° C. Mobile phase A (MPA) consists of water with 0.1% trifluoroacetic acid while mobile phase B (MPB) consists of 95% acetonitrile:5% water with 0.1% trifluoroacetic acid. Elution of the peptides is accomplished with a gradient from 0% to 47% MPB in 28 minutes followed by a ramp to 100% MPB in 4 minutes with a 5 minute hold at 100% MPB to wash the column. Re-equilibration of the column is performed by returning to 0% MPB in 1 minute followed by a 10 minute hold at 100% MPA. The flow rate is 0.6 mL/min and detection is accomplished by UV at 220 nm.

Figure 2:
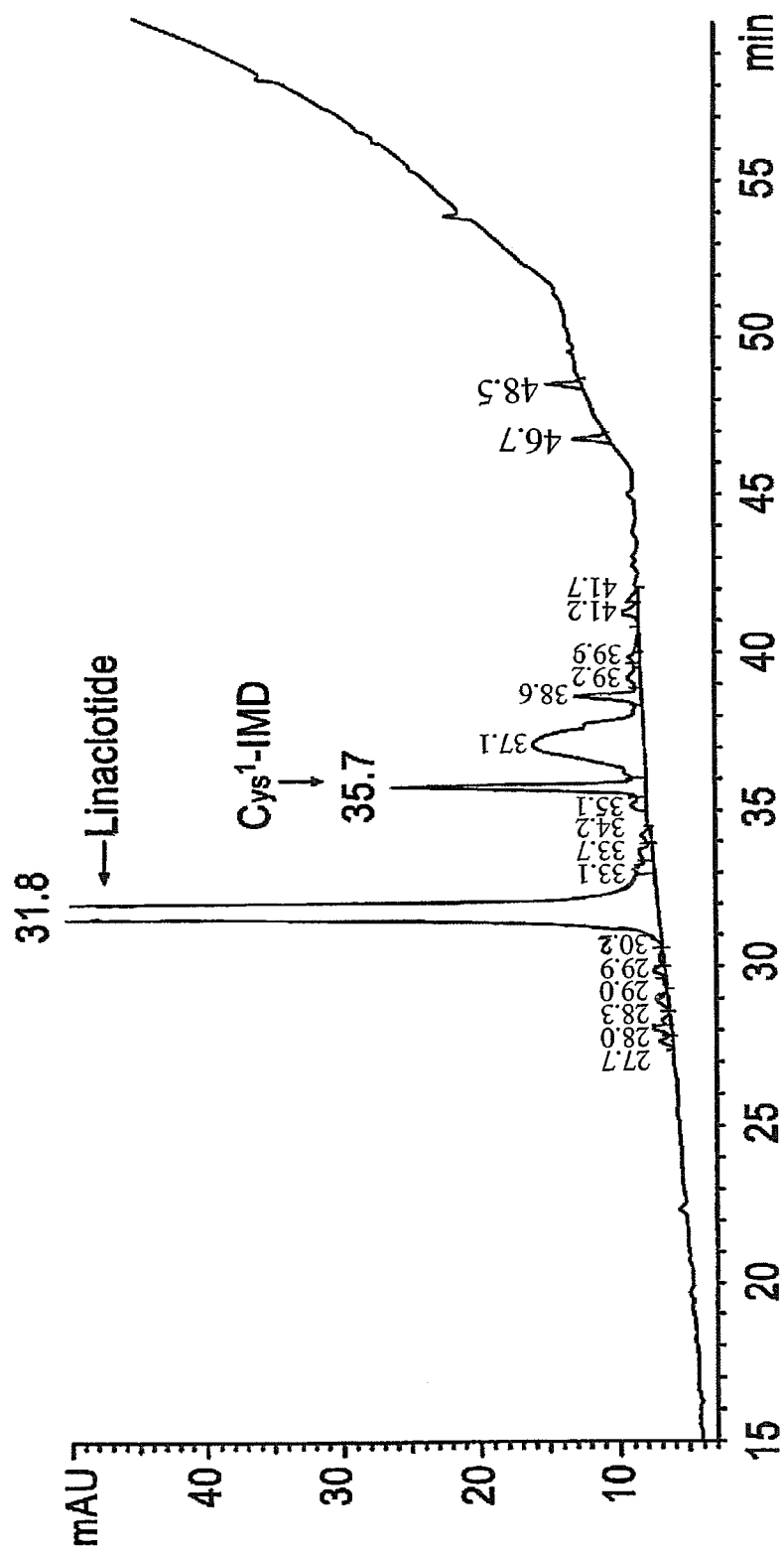
FIG. 2 demonstrates an example of an analysis of exemplary peptides by RP-HPLC, wherein "$Cys_1$-IMD" refers to the linaclotide imidazolidinone derivative modified on its N-terminal amine group.

Samples for analysis are prepared by addition of the contents of capsules of exemplary peptides to 0.1 N HCl to obtain a target concentration of 20 μg peptide/mL. 100 μL of this solution is injected onto the column. \
$Cys_1$-IMD Peptide The $Cys_1$-IMD peptide was purified using a 2-inch Waters C18 column with 0.1% TFA buffer with a linear gradient of 15-45% in 60 minutes of buffer B at flow rate of 100 mL/min. The pooled fractions with purity around 95% were loaded onto C18 column. After equilibrating the column with TEAP buffer and AA buffer, the peptide was purified and eluted out with HAC buffer with a linear gradient of 15-75% of buffer B in 60 minutes. Pooled fractions with purified peptide were lyophilized to dryness. An example of an analysis of linaclotide and $Cys_1$-IMD product by RP-HPLC is shown in FIG. 2.
$Glu_3$-Ethyl Ester Peptide The $Glu_3$-ethyl ester peptide (6.0 g) was dissolved in 12 L of 0.05M ammonium bicarbonate in water, and the oxidation process was monitored by Ellman's test, MS and analytical HPLC. The oxidation process took approximately 48 hours for completion.

The above solution was filtered and loaded onto a 2-inch C18 column, and purified by using 0.05M ammonium acetate buffer with a linear gradient of 10-40% of buffer B in 60 minutes at flow rate of 100 mL/min.

The pooled fractions with purity of >95% were lyophilized to dryness. After the peptides were dried, the peptide was re-dissolved in acetonitrile-water and acidified to pH around 4-5 by addition of acetic acid and re-lyophilized to dryness.
$Tyr_{14}$-Ethyl Ester Peptide The $Tyr_{14}$-ethyl ester peptide was purified by dissolving 2.5 g of the isolated peptide in 5 L of 0.05M ammonium bicarbonate in water, and the oxidation process was monitored by Ellman's test, MS and analytical HPLC. This oxidation process took approximately 16 hours for completion.
The above solution was filtered and loaded onto a 2-inch Polymer column, and purified by using 0.05M ammonium bicarbonate buffer with a linear gradient of 15-45% of buffer B in 60 minutes at flow rate of 100 mL/min. The pooled fractions with the peptide were lyophilized to dryness. After the peptide was dried, the peptide was re-dissolved in acetonitrile-water and acidified to pH 4-5 by addition of acetic acid and re-lyophilized to dryness.

The contents of the purified peptides were measured by determining the peptide concentration in the prepared sample against a similarly prepared external peptide standard.

Example 5

The effect of including various formaldehyde scavenger compounds on the stability of the linaclotide composition was next assessed.

60 cc square HPDE bottle (with 33 mm caps with induction seals) were loaded with (i) capsules containing beads coated with 145 μg or 290 μg of linaclotide, a binder, calcium chloride and leucine with an approximate molar ratio of $CaCl_2$:leucine:linaclotide of 60:30:1, (ii) either no formaldehyde scavenger compound (negative control) or a canister comprising one of the formaldehyde scavenger compounds disclosed in Table 3, and (iii) optionally a canister containing 3 grams of a silica gel desiccant.

In addition, some of the linaclotide compositions contained a formaldehyde stressor (in particular, an adhesive label on the desiccant canister that was applied by the manufacturer of the desiccant canister (Sud Chemie) (its presence in some linaclotide compositions is indicated in the table as "labeled canister"). Regarding the formaldehyde stressor canister, it was observed by applicants that the canister emits about 27.5 ug of formaldehyde in 24 hours at 60° C.

The linaclotide compositions were stored in a 40° C., 75% relative humidity stability chamber. Next, the quantity of $Cys_1$-IMD in each linaclotide composition was determined following 4, 8 and 13 week storage via Reverse Phase-HPLC using a gradient elution with UV detection at 220 nm. Quantitation was based on percent of chromatogram area.

Test samples of linaclotide capsules are prepared by emptying the bead contents into flasks, adding diluent and shaking for 30 minutes. The analysis used the bead contents of a composite of 6 or 8 capsules (for 290 μg and 145 μg, respectively). Operating conditions for the analytical test method by HPLC are outlined in Table 2. The results of the stability assay are set forth in Table 3.

TABLE 2

HPLC Purity and Degradation Conditions

| | | | |
|---|---|---|---|
| Mobile Phase A | 98:2:0.1 Water:Acetonitrile:TFA | | |
| Mobile Phase B | 95:5:0.1 Acetonitrile:Water:TFA | | |
| Diluent | 0.1 N Hydrochloric Acid | | |

| Gradient Profile | | | |
|---|---|---|---|
| Time (min) | % A | % B | Comments |
| 0 | 100 | 0 | Initial Conditions |
| 4 | 100 | 0 | 4-minute hold |
| 9 | 90 | 10 | 5-minute linear gradient |
| 43 | 77 | 23 | 34-minute linear gradient |
| 49 | 66 | 34 | 6-minute linear gradient |
| 59 | 20 | 80 | 10-minute linear gradient |
| 60 | 100 | 0 | Return to initial conditions |
| 67 | 100 | 0 | Re-equilibration |

| | |
|---|---|
| UV Detection | 220 nm |
| Injection Volume | 50 uL |
| Sample Concentration | 200 ug/mL |
| Column | YMC Pro C18, 150 mm × 3.0 mm ID, 3 um or equivalent |
| Column Temperature | 40° C. |
| Flow Rate | 0.6 mL/min |

TABLE 3

Effect of formaldehyde scavenger compounds on the Linaclotide Composition Stability

| Formaldehyde Scavenger Compound | % Cys$_1$-IMD after storage | | | % decrease in Cys$_1$-IMD as compared to negative control (after 13 weeks) |
|---|---|---|---|---|
| | 4 Weeks | 8 Weeks | 13 Week | |
| negative control (labeled canister with no scavenger) | 1.21 | 1.87 | 3.53 | — |
| d-meglumine (coated on beads in labeled canister) | 0.59 | 0.81 | 0.84 | −76% |
| histidine (coated on beads in labeled canister) | 0.60 | 0.68 | 1.00 | −72% |
| lyophilized leucine (in labeled canister) | 0.52 | 0.78 | 1.36 | −61% |
| asparagine (coated on beads in labeled canister) | 0.56 | 1.11 | 1.45 | −59% |
| glycine-leucine (coated on beads in labeled canister) | 0.61 | 1.03 | 1.51 | −57% |
| lysine (coated on beads in labeled canister) | 0.87 | 1.27 | 1.87 | −47% |
| glycine-glycine (coated on beads in labeled canister) | 0.89 | 1.40 | 1.98 | −44% |
| leucine (coated on beads in labeled canister) | 0.84 | 1.26 | 2.44 | −31% |
| aspartame (coated on beads in labeled canister) | 0.82 | 1.54 | 2.58 | −27% |

As is demonstrated in Table 3, linaclotide compositions that contained formaldehyde scavenger compounds exhibited surprisingly and unexpectedly higher stability that those not containing a formaldehyde scavenger compound (negative control).

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A linaclotide composition comprising linaclotide, a sterically hindered primary amine, a divalent metal cation and a formaldehyde scavenger compound and further comprises a peptide having the structure of formula (I) or a pharmaceutically acceptable salt thereof (SEQ ID NO: 3):

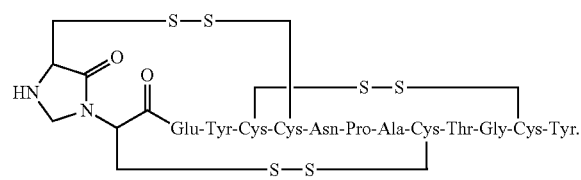

(I)

2. The composition of claim 1, wherein the linaclotide composition comprises the peptide of formula (I) in a concentration of up to 5% by weight as compared to the weight of linaclotide.

3. The composition of claim 1, wherein the linaclotide composition comprises the peptide of formula (I) in a concentration of up to 3% by weight as compared to the weight of linaclotide.

4. The composition of claim 1, wherein the linaclotide composition comprises the peptide of formula (I) in a concentration of up to 2% by weight as compared to the weight of linaclotide.

5. The composition of claim 1, wherein the linaclotide composition comprises the peptide of formula (I) in a concentration of up to 1% by weight as compared to the weight of linaclotide.

6. The composition of claim 1 comprising a formaldehyde scavenger compound and an oral pharmaceutical dosage form comprising about 145 μg or about 290 μg of linaclotide or a pharmaceutically acceptable salt thereof, Ca²⁺ or a salt thereof, leucine, and a peptide having the structure of formula (I) or a pharmaceutically acceptable salt thereof (SEQ ID NO: 3):

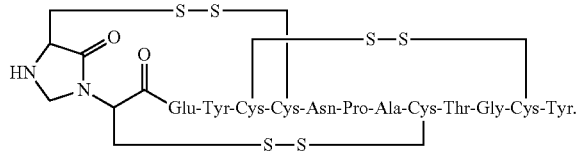

(I)

7. The composition of claim 6, wherein the peptide of formula (I) is present in the oral pharmaceutical dosage form in an amount of about 0.001 to about 2 wt. % relative to the total weight of the dosage form.

8. The composition of claim 6, wherein the peptide of formula (I) is present in the oral pharmaceutical dosage form in an amount of about 0.001 to about 1 wt. % relative to the total weight of the dosage form.

9. The composition of claim 6, wherein the peptide of formula (I) is present in the oral pharmaceutical dosage form in an amount of about 0.001 to about 0.75 wt. % relative to the total weight of the dosage form.

10. The composition of claim 6, wherein the peptide of formula (I) is present in the oral pharmaceutical dosage form in an amount of about 0.001 to about 0.5 wt. % relative to the total weight of the dosage form.

11. The composition of claim 1, wherein the divalent metal cation is Ca²⁺ or a salt thereof, the sterically hindered primary amine is leucine, and wherein the linaclotide composition comprises a molar ratio of divalent metal cation:sterically hindered primary amine:linaclotide of about 57-63:28-32:1.

12. The composition of claim 6, wherein the Ca²⁺ or a salt thereof and leucine are present in the oral pharmaceutical dosage form in a molar ratio of Ca²⁺:leucine:linaclotide of about 57-63:28-32:1.

13. The composition of claim 8, wherein the Ca²⁺ or a salt thereof and leucine are present in the oral pharmaceutical dosage form in a molar ratio of Ca²⁺:leucine:linaclotide of about 57-63:28-32:1.

14. The composition of claim 9, wherein the Ca²⁺ or a salt thereof and leucine are present in the oral pharmaceutical dosage form in a molar ratio of Ca²⁺:leucine:linaclotide of about 57-63:28-32:1.

15. The composition of claim 10, wherein the Ca²⁺ or a salt thereof and leucine are present in the oral pharmaceutical dosage form in a molar ratio of Ca²⁺:leucine:linaclotide of about 57-63:28-32:1.

16. The composition of claim 8, wherein the oral pharmaceutical dosage form further comprises an oxidation product having a structure of (SEQ ID NO: 4):

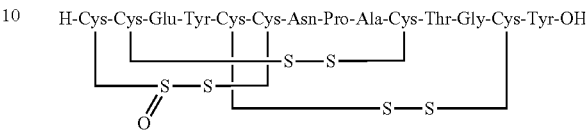

in an amount from about 0.05% to about 5% by weight relative to the total weight of the dosage form.

17. The composition of claim 16, wherein the oxidation product in present in the dosage form in an amount of about 0.05% to about 2% relative to the total weight of the dosage form.

18. The composition of claim 16, wherein the oxidation product in present in the dosage form in an amount of about 0.05% to about 1% relative to the total weight of the dosage form.

19. The composition of claim 6, wherein the Ca²⁺ or a salt thereof and leucine are present in the oral pharmaceutical dosage form in a molar ratio of Ca²⁺:leucine:linaclotide of about 57-63:28-32:1, wherein the formaldehyde scavenger compound is selected from the group consisting of d-meglumine and histidine, and wherein the peptide of formula (I) is present in the oral pharmaceutical dosage form in an amount of about 0.001 to about 1 wt. % relative to the total weight of the dosage form.

20. The composition of claim 19, wherein the peptide of formula (I) is present in the oral pharmaceutical dosage form in an amount of about 0.001 to about 0.75 wt. % relative to the total weight of the dosage form.

21. The composition of claim 19, wherein the peptide of formula (I) is present in the oral pharmaceutical dosage form in an amount of about 0.001 to about 0.5 wt. % relative to the total weight of the dosage form.

22. The composition of claim 1, wherein the formaldehyde scavenger compound is d-meglumine.

* * * * *

SEQUENCE LISTING

```
<160> NUMBER OF SEQ ID NOS: 24

<210> SEQ ID NO 1
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 1

Cys Cys Glu Tyr Cys Cys Asn Pro Ala Cys Thr Gly Cys Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
```

```
<222> LOCATION: (1)..(1)
<223> OTHER INFORMATION: Xaa is a Cys, wherein the alpha-amine of the
      Cys is deaminated
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 2

Xaa Cys Glu Tyr Cys Cys Asn Pro Ala Cys Thr Gly Cys Tyr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa is a cysteine modified into an
      imidazolidinone
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 3

Xaa Cys Glu Tyr Cys Cys Asn Pro Ala Cys Thr Gly Cys Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Cys1 sulfur atom is oxidized
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 4

Cys Cys Glu Tyr Cys Cys Asn Pro Ala Cys Thr Gly Cys Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetically generated peptide
<220> FEATURE:
```

```
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu2 residue is esterified with C1-C6 alkyl
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: C-terminus is esterified with C1-C6 alkyl

<400> SEQUENCE: 5

Cys Cys Glu Tyr Cys Cys Asn Pro Ala Cys Thr Gly Cys Tyr
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu3 is esterified with C1-C6 alkyl
<220> FEATURE:
<221> NAME/KEY: DISULFID
<222> LOCATION: (5)..(13)

<400> SEQUENCE: 6

Cys Cys Glu Tyr Cys Cys Asn Pro Ala Cys Thr Gly Cys Tyr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: C-terminus is esterified with C1-C6 alkyl

<400> SEQUENCE: 7

Cys Cys Glu Tyr Cys Cys Asn Pro Ala Cys Thr Gly Cys Tyr
1               5                   10

<210> SEQ ID NO 8
<211> LENGTH: 14
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa is a cysteine with an N-terminal imine
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 8

Xaa Cys Glu Tyr Cys Cys Asn Pro Ala Cys Thr Gly Cys Tyr
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu3 contains a methyl ester
<220> FEATURE:
<221> NAME/KEY: DISULFID
<222> LOCATION: (5)..(13)

<400> SEQUENCE: 9

Cys Cys Glu Tyr Cys Cys Asn Pro Ala Cys Thr Gly Cys Tyr
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu3 contains an ethyl ester
<220> FEATURE:
<221> NAME/KEY: DISULFID
<222> LOCATION: (5)..(13)

<400> SEQUENCE: 10

Cys Cys Glu Tyr Cys Cys Asn Pro Ala Cys Thr Gly Cys Tyr
1               5                   10

<210> SEQ ID NO 11
<211> LENGTH: 14
<212> TYPE: PRT
<213> ORGANISM: Artificial Sequence
<220> FEATURE:
```

```
<223> OTHER INFORMATION: Synthetically generated peptide
<220> FEATURE:
<221> NAME/KEY: DISULFID
<222> LOCATION: (1)..(5)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu3 contains a propyl ester
<220> FEATURE:
<221> NAME/KEY: DISULFID
<222> LOCATION: (5)..(13)

<400> SEQUENCE: 11

Cys Cys Glu Tyr Cys Cys Asn Pro Ala Cys Thr Gly Cys Tyr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(5)
<220> FEATURE:
<221> NAME/KEY: DISULFID
<222> LOCATION: (2)..(10)
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: Tyr14 (C-terminus) contains a methyl ester

<400> SEQUENCE: 12

Cys Cys Glu Tyr Cys Cys Asn Pro Ala Cys Thr Gly Cys Tyr
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: Tyr14 (C-terminus) contains an ethyl ester

<400> SEQUENCE: 13

Cys Cys Glu Tyr Cys Cys Asn Pro Ala Cys Thr Gly Cys Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetically generated peptide
```

```
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: Tyr14 (C-terminus) contains a propyl ester

<400> SEQUENCE: 14

Cys Cys Glu Tyr Cys Cys Asn Pro Ala Cys Thr Gly Cys Tyr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu3 contains a methyl ester
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: Tyr14 (C-terminus) contains a methyl ester

<400> SEQUENCE: 15

Cys Cys Glu Tyr Cys Cys Asn Pro Ala Cys Thr Gly Cys Tyr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu3 contains an ethyl ester
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: Tyr14 (C-terminus) contains an ethyl ester

<400> SEQUENCE: 16

Cys Cys Glu Tyr Cys Cys Asn Pro Ala Cys Thr Gly Cys Tyr
1               5                   10
```

```
<210> SEQ ID NO 17
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Glu3 contains a propyl ester
<220> FEATURE:
<221> NAME/KEY: DISULFID
<222> LOCATION: (5)..(13)
<220> FEATURE:
<221> NAME/KEY: MISC_FEATURE
<222> LOCATION: (14)..(14)
<223> OTHER INFORMATION: Tyr14 (C-terminus) contains a propyl ester

<400> SEQUENCE: 17

Cys Cys Glu Tyr Cys Cys Asn Pro Ala Cys Thr Gly Cys Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa is a cysteine, wherein the cysteine is
      deaminated and the alpha ketone is in geminal diol form
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 18

Xaa Cys Glu Tyr Cys Cys Asn Pro Ala Cys Thr Gly Cys Tyr
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(3)
<223> OTHER INFORMATION: Either or both of Glu3 and Tyr14 are alkylated
      with C1-C6 alkyl
<220> FEATURE:
<221> NAME/KEY: DISULFID
<222> LOCATION: (5)..(13)
<220> FEATURE:
```

```
<221> NAME/KEY: MISC_FEATURE
<222> LOCATION: (14)..(14)
<223> OTHER INFORMATION: Either or both of Glu3 and Tyr14 are alkylated
      with C1-C6 alkyl

<400> SEQUENCE: 19

Cys Cys Glu Tyr Cys Cys Asn Pro Ala Cys Thr Gly Cys Tyr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 20

Cys Cys Glu Tyr Cys Cys Asn Pro Ala Cys Thr Gly Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 21

Cys Cys Glu Tyr Cys Cys Asp Pro Ala Cys Thr Gly Cys Tyr
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (5)..(5)
<223> OTHER INFORMATION: Cy5 is D-Cys
<220> FEATURE:
```

```
<221> NAME/KEY: DISULFID
<222> LOCATION: (5)..(13)

<400> SEQUENCE: 22

Cys Cys Glu Tyr Cys Cys Asn Pro Ala Cys Thr Gly Cys Tyr
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (5)..(13)
<223> OTHER INFORMATION: Cys5-Cys13 contains a trisulfide bond

<400> SEQUENCE: 23

Cys Cys Glu Tyr Cys Cys Asn Pro Ala Cys Thr Gly Cys Tyr
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 24

Cys Cys Glu Tyr Cys Cys Asn Pro Ala Cys Thr Gly Cys Tyr
1               5                   10
```